US007766482B2

(12) United States Patent
Smith, III et al.

(10) Patent No.: US 7,766,482 B2
(45) Date of Patent: Aug. 3, 2010

(54) METHODS AND APPARATUSES FOR ALTERING RELATIVE CURVATURE OF FIELD AND POSITIONS OF PERIPHERAL, OFF-AXIS FOCAL POSITIONS

(75) Inventors: Earl Leo Smith, III, Houston, TX (US); Nelson Greeman, Jr., San Antonio, TX (US); Patsy Greeman, legal representative, San Antonio, TX (US); Arthur Ho, Coogee (AU); Brien Anthony Holden, Kingsford (AU)

(73) Assignee: Vision CRC Limited, Sydney, New South Wales (AU)

( * ) Notice: Subject to any disclaimer, the term of this patent is extended or adjusted under 35 U.S.C. 154(b) by 0 days.

(21) Appl. No.: 12/399,207

(22) Filed: Mar. 6, 2009

(65) Prior Publication Data

US 2009/0161065 A1 Jun. 25, 2009

Related U.S. Application Data

(63) Continuation of application No. 11/349,295, filed on Feb. 7, 2006, now Pat. No. 7,503,655, which is a continuation-in-part of application No. 10/887,753, filed on Jul. 9, 2004, now Pat. No. 7,025,460.

(60) Provisional application No. 60/523,533, filed on Nov. 19, 2003.

(51) Int. Cl.
*A61B 3/10* (2006.01)
(52) U.S. Cl. .................................................. 351/246
(58) Field of Classification Search ................. 351/221, 351/205, 200, 246, 247
See application file for complete search history.

(56) References Cited

U.S. PATENT DOCUMENTS

| 5,695,509 | A | | 12/1997 | El Hage |
| 5,838,419 | A | * | 11/1998 | Holland ..................... 351/177 |
| 6,045,578 | A | * | 4/2000 | Collins et al. ................ 623/4.1 |
| 6,312,424 | B1 | | 11/2001 | Largent |
| 6,547,393 | B2 | | 4/2003 | Ruiz |
| 6,659,613 | B2 | | 12/2003 | Applegate et al. |
| 6,752,499 | B2 | * | 6/2004 | Aller .......................... 351/247 |
| 6,905,210 | B2 | | 6/2005 | Applegate et al. |
| 7,025,460 | B2 | * | 4/2006 | Smitth et al. ................ 351/221 |
| 7,503,655 | B2 | * | 3/2009 | Smith et al. ................ 351/246 |
| 2001/0016731 | A1 | | 8/2001 | DeVore et al. |
| 2002/0075451 | A1 | | 6/2002 | Ruiz |

OTHER PUBLICATIONS

International Preliminary Report on Patentability mailed on May 22, 2006 in PCT/US2004/022083.

(Continued)

*Primary Examiner*—Hung X Dang
(74) *Attorney, Agent, or Firm*—Smith Moore Leatherwood LLP

(57) ABSTRACT

A method and apparatus are disclosed for controlling optical aberrations to alter relative curvature of field by providing ocular apparatuses, systems and methods comprising a predetermined corrective factor to produce at least one substantially corrective stimulus for repositioning peripheral, off-axis, focal points relative to the central, on-axis or axial focal point while maintaining the positioning of the central, on-axis or axial focal point on the retina. The invention will be used to provide continuous, useful clear visual images while simultaneously retarding or abating the progression of myopia or hypermetropia.

2 Claims, 29 Drawing Sheets

OTHER PUBLICATIONS

International Search Report mailed on Apr. 10, 2004 in PCT/US2004/022083.

Written Opinion mailed on Apr. 10, 2004 in PCT/US2004/022083.

* cited by examiner

Figures 15a to 15d.
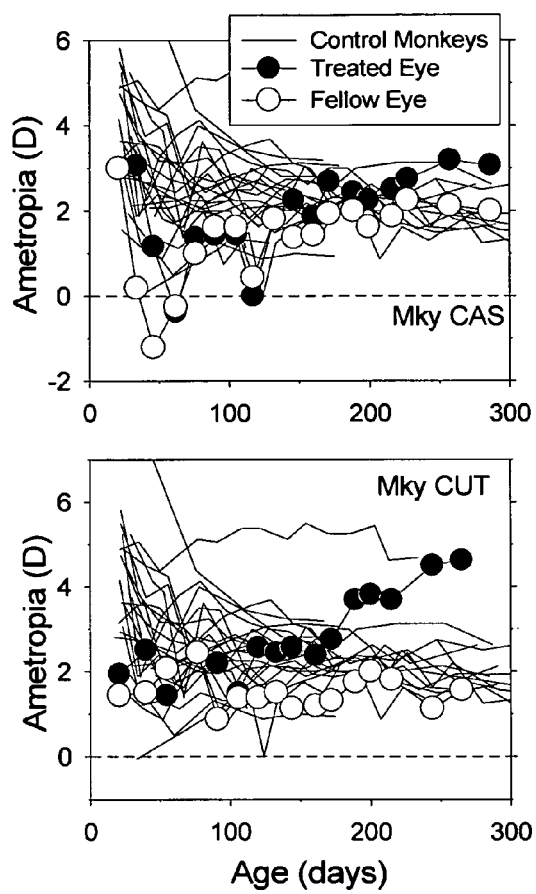
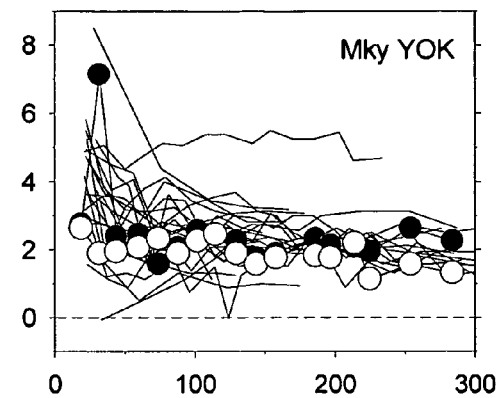
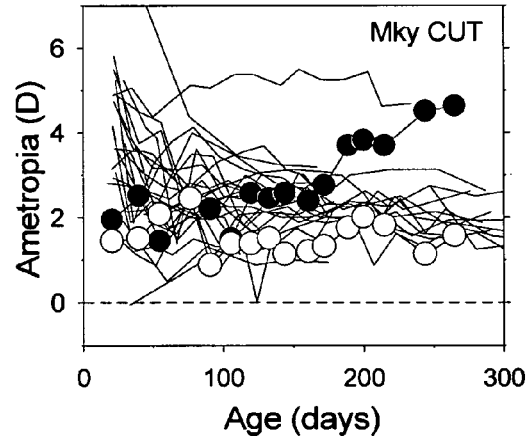
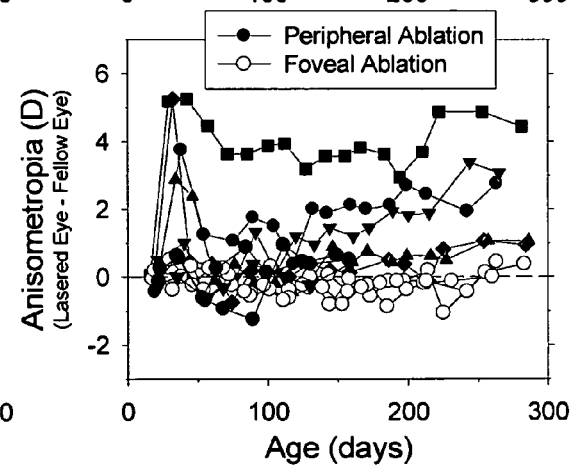
Figure 15a
Figure 15b
Figure 15c
Figure 15d Figures 17a to 17d.
Figure 17a
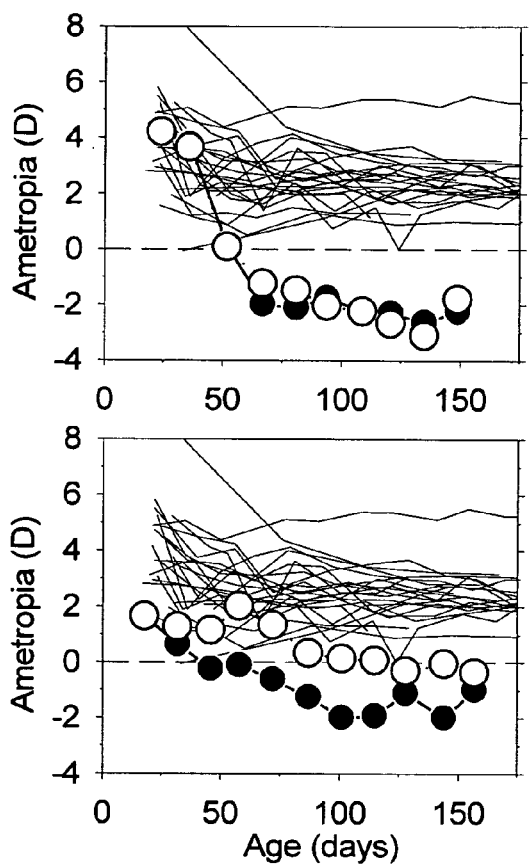
Figure 17b
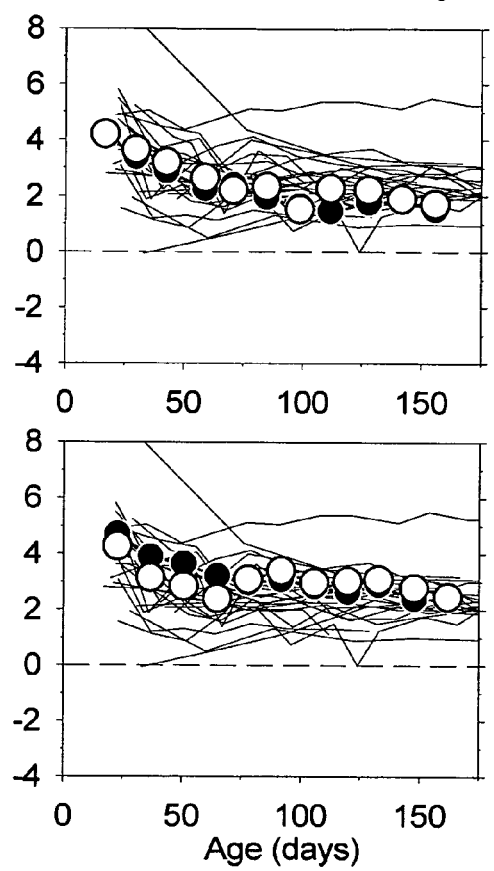
Figure 17c
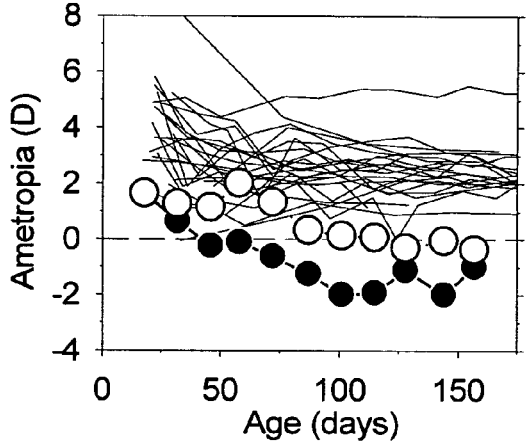
Figure 17d
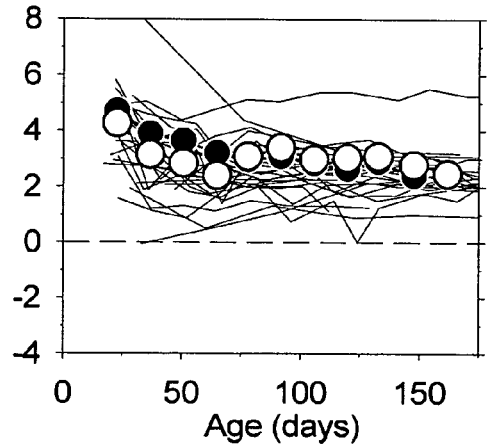

METHODS AND APPARATUSES FOR ALTERING RELATIVE CURVATURE OF FIELD AND POSITIONS OF PERIPHERAL, OFF-AXIS FOCAL POSITIONS

RELATED APPLICATION DATA

This application is continuation of U.S. patent application Ser. No. 11/349,295 filed Feb. 7, 2006, now U.S. Pat. No. 7,503,655, which is a continuation-in-part of U.S. patent application Ser. No. 10/887,753, filed Jul. 9, 2004, now U.S. Pat. No. 7,025,460, which claims the benefit of U.S. Provisional Application No. 60/523,533 filed Nov. 19, 2003, the contents of each of which are incorporated herewith by reference.

FIELD OF THE INVENTION

The present invention is directed to methods and apparatuses for retarding or eliminating the progression of myopia (short-sightedness) in an individual by controlling off-axis (peripheral) aberrations, thereby manipulating the curvature of field of a visual image while simultaneously providing clear central imaging.

BACKGROUND OF THE INVENTION

The prevalence of myopia (short sightedness) is increasing rapidly. Studies, for example, have shown a dramatic rise in the incidence of myopia (−0.25 D or more) in 7 year old Taiwanese children, from 4% to 16% between 1986 and 2000, and the prevalence of myopia (−0.25 D or more) in Taiwanese school children aged 16 to 18 years is as high as 84%. A population-based study in Mainland China reports that 55% of girls and 37% of boys at the age of 15 have significant myopia (−1.00 D or more).

Studies show that 50% of people with high myopia (over −6.00 D) have some form of retinal pathology. Myopia significantly increases the risk of retinal detachment, (depending on the level of myopia), posterior cataract and glaucoma. The optical, visual and potential pathological effects of myopia and its consequent inconvenience and cost to the individual and community, makes it desirable to have effective strategies to slow the progress, or prevent or delay the onset of myopia, or limit the amount of myopia occurring in both children and young adults.

Thus, a large percentage of the world's population has myopia at a level that requires some form of optical correction in order to see clearly. It is known that myopia, regardless of age of onset, tends to increase in amount requiring stronger and stronger correction. These corrections are available through a wide range of devices including spectacles, contact lenses and refractive surgery. These corrections, however, do little if anything to slow or stop the progression of myopia and arguably, according to some research findings, actually promote the progression of myopia.

One form of myopia, (often called "congenital myopia"), occurs at birth, is usually of high level, and may become progressively worse. A second type (sometimes called "juvenile myopia" or "school myopia") begins in children at age 5 to 10 years and progresses through to adulthood or sometimes beyond. A third 'type' of myopia (which may be referred to as "adult myopia") begins in young adulthood or late teenage years (16 to 19 years of age) and increases during adulthood, sometimes leveling off and at other times continuing to increase.

Strategies to prevent or slow myopia have been suggested that involve pharmacological interventions with anti-muscarinic drugs such as atropine (that are usually used to paralyze accommodation), or pirenzepine. However, the potential disadvantages associated with the long-term use of such pharmacological substances may render such modalities problematical.

It is known that during early development, the two eyes typically grow in a highly coordinated manner toward the ideal optical state, a process referred to as "emmetropization". From the standpoint of optical intervention to prevent the onset, or retard the progression of myopia, three fundamental observations, which have been made in a variety of vertebrate animals ranging from birds to higher primates, have demonstrated conclusively that the emmetropization process is actively regulated by visual feedback.

First, conditions or experimental manipulations that prevent the formation of a clear retinal image cause the eye to grow abnormally long (called "axial elongation") and to become myopic or short-sighted, a phenomenon referred to as "form-deprivation myopia".

Second, if an eye that has form-deprivation myopia is subsequently allowed unrestricted vision, that eye then grows in a manner that eliminates the existing refractive error. This recovery requires visual feedback associated with the eye's effective refractive error because optically correcting the myopic error with spectacle lenses prevents recovery.

Third, imposing a refractive error on a normal eye (or "emmetropic" eye, one that is neither short-sighted nor long-sighted) with a spectacle lens produces compensating ocular growth that eliminates the refractive error produced by viewing through the lens, a phenomenon called "lens compensation". Either myopia or hypermetropia (long-sightedness) can be induced in a variety of animal models including higher primates by the wearing of negatively-powered or positively-powered spectacle lenses, respectively. For example, when the image is positioned by the use of negative-powered lens to a position posterior to (i.e. behind) the retina, for example, myopia is induced. This myopia progression is actuated by axial elongation (growth bringing about a 'lengthening' of the eye-ball).

Thus, the mechanisms that are responsible for emmetropization monitor the retinal image and adjust axial growth rates to eliminate refractive errors. That is, the eye uses optical defocus to guide eye growth toward the ideal optical state.

For reasons that are not entirely understood, the emmetropization process goes awry in some individuals resulting in common refractive errors like myopia. Research using animal models strongly suggests that optical defocus could play a role in this process. Yet, to date treatment strategies for myopia that have manipulated the effective focus of the eye for central vision (e.g., bifocals) have had only limited success in preventing myopia or slowing down the progression of myopia.

For example, bifocal or progressive spectacle lenses or bifocal contact lenses have long been regarded as potential strategies for retarding the progress of myopia. However, studies on their efficacy show only limited efficacy. In the case of spectacle bifocals, compliance of the wearer to always look through the near addition portion for near work cannot be guaranteed. The bifocal contact lenses that have been used to date have been simultaneous vision bifocals. Such bifocals degrade the overall retinal image quality and are known to produce visual problems such as haloes, glare and ghosting, making them undesirable for the wearers.

Additional studies have shown that interrupting myopia-inducing stimuli, for even relatively short periods of time, reduces or even eliminates the myopia-inducing effects of such stimuli. The implication is that a 'daily-wear' approach, whereby the myope ceases to use the myopia-reduction device for certain periods during the day (e.g. removal after work and before sleep), would not be efficient and may well compromise its efficacy.

Another optical method, used in attempts to retard the progression of myopia in individuals is "under-correction". In under-correction, the wearer is prescribed and provided with a correction (e.g. spectacles, or contact lenses) that is lower in amount than the full refractive prescription required for clear vision. For example, a −4.00 D myope may be given only a −3.50 D pair of spectacles rendering this myope still −0.50 D relatively myopic. Therefore, this method implicitly requires the central foveal visual image (the most important area for critical vision, e.g. visual acuity) to be blurred or degraded in some way. This significantly detracts from the usefulness of the device as the wearer is constantly reduced in visual performance, (e.g. preventing the wearer from driving due to legal vision requirements). Further, there is evidence to suggest that an under-correction approach may even accelerate myopia progression in some individuals.

A means of abating, retarding, and ultimately reversing, the progression of myopia, would provide enormous benefits to the millions of people who suffer from myopia as well as reduce the cost to individuals, health care workers and providers, and governments associated with myopia.

SUMMARY OF THE INVENTION

To date, treatment strategies for myopia that have manipulated the effective focus of the eye for central vision (e.g. bifocals) have had only limited success in preventing myopia or slowing down the progression of myopia. These previous efforts to prevent myopia and myopic progression have implicitly assumed that eye growth is dominated by visual feedback associated with central vision and that, by further implication, vision-dependent mechanisms located in the center of the retina (i.e. the fovea of the eye) control refractive development. Indeed, in light of the discoveries reported herein, in conjunction with the present invention, it is now believed that known, conventional devices that do not control curvature of field, could be contributing to, or even causing, myopia and are therefore at least disadvantageous, and potentially harmful in terms of myopia development.

Our present invention provides a method of abating, retarding or eliminating the progression of myopia or hypermetropia in an individual by controlling off-axis aberrations, through manipulating the curvature of field of a visual image in a predetermined fashion and ultimately altering, reducing or eliminating eye axial elongation.

This present invention is based on new learning from our experiments that demonstrates that the peripheral retinal image (i.e. peripheral vision) plays a major role in determining overall eye length, and is an effective stimulus that promotes peripheral and total eye growth that results in axial elongation, an overall increase in eye size and myopia.

The present invention is also directed to a method by which myopia progression may be retarded (and in many cases, halted or reversed) with the use of a novel optical device having a predetermined off-axis aberration controlled design that abates, retards or eliminates eye growth.

Further, according to the present invention, the progression of myopia is modified by precise, predetermined control of the off-axis optical corrective factors, or aberrations of the corrective device, or the combined off-axis optical aberrations of the eye and corrective device, such that the visual image has a peripheral field image location that is positioned more anteriorly to (or in front of) the peripheral retina (i.e. towards the cornea or the front of the eye) than normally in the uncorrected condition or with traditional correction devices or strategies while the central field image location is positioned near the central retina (i.e. the fovea). This arrangement minimizes or eliminates the stimulus for eye axial elongation leading to myopia. And since the device does not introduce any central field defocusing (as are, for example, introduced by under-correction methods, or bifocal or progressive optical devices) the devices of the present invention provide the wearer with good visual acuity. Thus, the invention offers the benefits of retarding progression of refractive error while substantially simultaneously maintaining a clear, useful critical vision for the wearer.

For purposes of clarity, according to the present invention, the term "in front of" orientationally reflects the concept that a point is located at a lesser distance in a direction measured from the cornea towards the retina than its comparative point, while the term "behind" reflects the concept that a point is located at a greater distance from the cornea towards the retina than its comparative point.

The aberration control method of the present invention for treating myopia may be implemented by employing, for example, spectacles, contact lenses, corneal implants (e.g. on-lays or in-lays), anterior chamber lenses, and intraocular lenses (IOL), as well as any corneal or epithelial sculpting or remodeling procedures including orthokeratology (which is a specialized method employing contact lenses for temporarily changing the refractive state of the eye through corneal and epithelial remodeling by the short-term wearing of contact lenses of specific designs) and any refractive surgical procedures (e.g. epikeratophakia, thermo-keratoplasty, LASIK, PRK, LASEK), alone or in combination.

Preferably, the methods and devices of the present invention are implemented in a modality that can remain substantially co-axial with (i.e. maintain axial alignment with, or maintain "centration" with) the eye, regardless of the direction of gaze of the eye, such as orthokeratology, corneal refractive surgery, corneal implants, contact lenses and intraocular lenses. In this way, the precise control of peripheral aberrations leading to the precise, predetermined manipulation of the curvature of field could be predictably maintained irrespective of eye movement.

Also preferably, the devices of the present invention are those that are positioned away from the nodal point of the eye so as to render manipulation of peripheral aberration, suitable for control of myopia, with greater degrees of freedom and effectiveness. Such devices include spectacles, contact lenses including lenses used in an orthokeratology modality and corneal implants.

Also preferably, the methods and devices of the present invention are implemented in a modality, which can be presented to the eye substantially in a relatively continuous manner so that it is available during all open-eye occasions, such as continuous wear contact lenses (e.g. soft, RGP, scleral haptic), orthokeratology, corneal refractive surgery, corneal implants, anterior chamber lenses and intraocular lenses. By providing a substantially continuous visual stimulus, without interruption, maximal effectiveness of the myopia treatment can be achieved.

Also preferably, the present invention is implemented in spectacles, contact lens (soft, rigid gas permeable also abbreviated as "RGP", scleral haptic), orthokeratology or corneal on-lay modality, since changes in power and peripheral aberration profiles (required as the wearer's amount of myopia changes) can be readily made without for example, the repeated need for invasive intraocular surgery.

In the case of spectacles, contact lenses or orthokeratology, a new lens can be prescribed and dispensed readily.

For the on-lay, the corneal epithelium is scraped away, the existing on-lay removed and a new on-lay affixed in place with the epithelium allowed to re-grow over the device.

The present invention is particularly suited for use in an extended wear or continuous wear contact lens modality, orthokeratology modality or a corneal on-lay modality, thus providing a substantially continuous stimulus for myopia retardation.

Typically, extended wear or continuous wear contact lenses, which may be, for example, soft or RGP lenses, have sufficient oxygen permeability and other properties to permit the lens to be left in the eye during sleep yet still transfer sufficient oxygen from the tarsal conjunctiva to the cornea to maintain ocular health, despite atmospheric oxygen not being available due to the closed eye-lid.

In orthokeratology, the contact lens (which may also be of the high oxygen permeability kind suitable for extended or overnight wear) may be worn for a short period (e.g. during sleeping hours) to remodel the epithelium and cornea after which the contact lens may be removed leaving the patient in the desired refractive and optical aberration state according to the present invention without contact lens wear for the period of effectiveness of the orthokeratology.

The present invention can be realized in a number of ways to retard or eliminate myopia. Principally, an optical vision correction device is designed with the necessary amount of refractive power to correct central vision to which a prescribed amount of suitable off-axis or peripheral aberrations, in particular relative curvature of field, is incorporated. This off-axis peripheral aberration or relative curvature of field, introduced together with the appropriate refractive power is precisely manipulated so that, in combination with the existing ocular aberrations, the image at the peripheral field is positioned more anteriorly than the corresponding position of the peripheral retina while the central image is positioned at or near the fovea. Typically, due to the presence of radial astigmatism (a type of peripheral, off-axis aberration), two line foci are associated with the peripheral image (the interval between the two line foci is called the "interval of Sturm" which also includes the "circle of least confusion", a position along the interval of Sturm which produces the minimal focal spot diameter and is generally considered the position of best equivalent focus). In the presence of radial astigmatism, the curvature of field introduced according to the present invention (together with the appropriate refractive power) is manipulated so that, in combination with the ocular aberrations, at least the more anterior line focus associated with radial astigmatism is positioned more anteriorly than the peripheral retina so that a part of, or in some cases the entirety of, the interval of Sturm lies in front of the peripheral retina while the central image is positioned at or near the fovea.

A particularly beneficial arrangement can be realized when the curvature of field is manipulated so that the more posterior line focus associated with radial astigmatism is focused near or on the retina. In this particular arrangement the peripheral retinal images would also be in focus in respect to the astigmatism as one of the two line foci of astigmatism will be placed near the retina.

These arrangements provide continuously clear central vision, and particularly, good central visual acuity for the wearer while simultaneously retarding or eliminating the progression of myopia in myopes, or preventing the initiation of myopia in non-myopes (emmetropes or hypermetropes) with myopic tendencies (i.e. individuals with a predisposition to develop myopia).

BRIEF DESCRIPTION OF THE DRAWINGS

FIGS. 4a and 4b illustrate the conventional approach for myopia treatment, in particular under-correction, which addresses only the on-axis or central field refractive state. FIGS. 4c to 4d describe our experiments, which demonstrate the important role of the peripheral field in the control, development, progression and regression of myopia. FIGS. 4e and 4f detail the principle of the present invention and the effect of relative curvature of field in the control of progression of myopia. FIGS. 4g and 4h explain, under the principle of the present invention, the basis for the relative inefficacy of under-correction approaches. FIGS. 4i to 4l detail the principle of the present invention for the case of an eye with existing positive relative curvature of field.

FIGS. 6a and 6b illustrate a design for pronounced altering of the relative curvature of field wherein both sagittal and tangential line foci associated with radial astigmatism are repositioned to in front of the peripheral retina. FIGS. 6c and 6d illustrate a design for a more subtle altering of the relative curvature of field wherein the sagittal line foci associated with radial astigmatism is repositioned to lie on or slightly in front of the peripheral retina.

FIG. 7a is a contact lens design diagram showing front and back surface profile and thickness profile along a half-meridian, and FIG. 7b is a computer-assisted optical ray-tracing program output in the form of a relative field curvature graph illustrating the design and relative curvature of field performance of a soft contact lens of the present invention suitable for retarding, ceasing or reversing the progression of myopia in a −3 D myope.

FIG. 8a is a contact lens design diagram and FIG. 8b a computed relative field curvature graph illustrating the design and relative curvature of field performance of a soft contact lens of the present invention suitable for retarding, ceasing or reversing the progression of myopia in a −10 D myope.

FIGS. 15a to 15d illustrate the results of procedures performed upon the mid- to far-peripheral retinas according to the procedures outlined in Example 3.

FIGS. 17a to 17d illustrate the results of procedures performed using negative-powered and positive-powered lenses according to the procedures outlined in Example 5.

DETAILED DESCRIPTION OF THE INVENTION

Figure 1A:
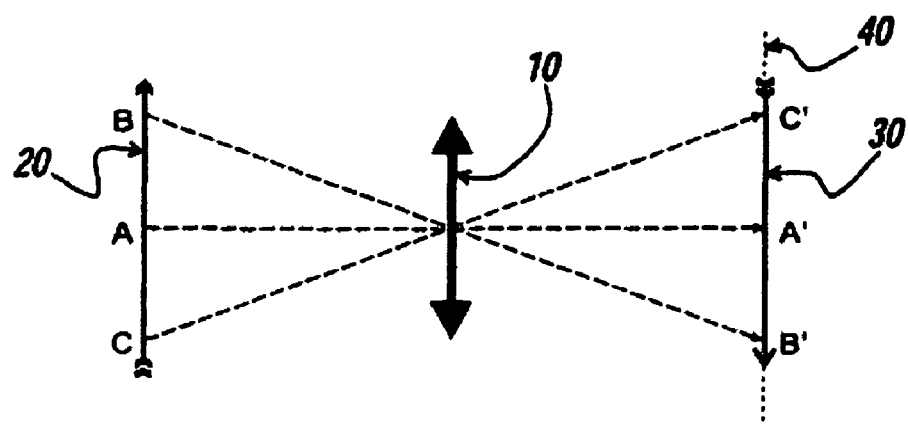
FIGS. 1a to 1c are optical diagrams explaining the off-axis, peripheral aberration of curvature of field for a general optical system.

During early development the two eyes typically grow in a highly coordinated manner toward the ideal optical state, a process referred to as "emmetropization". Three fundamental observations, which have been made in a wide variety of vertebrate animals ranging from birds to higher primates, have demonstrated conclusively that the emmetropization process is actively regulated by visual feedback. First, conditions or experimental manipulations that prevent the formation of an adequately clear retinal image cause the eye to grow abnormally long and to become myopic or short-sighted, a phenomenon referred to as "form-deprivation" myopia. Second, if an eye that has form-deprivation myopia is subsequently allowed unrestricted vision, that eye then grows in a manner that eliminates the existing refractive error. This recovery requires visual feedback associated with the eye's effective refractive error because optically correcting the myopic error with spectacle lenses prevents recovery. Third, imposing a refractive error on a normal eye with a spectacle lens produces compensating ocular growth that eliminates the refractive error produced by the lens, a phenomenon sometimes called "lens compensation".

Thus, the mechanisms that are responsible for emmetropization monitor the retinal image and adjust axial growth to eliminate refractive errors. That is, the eye uses optical defocus to guide eye growth towards the ideal optical state.

For reasons that are not entirely understood the emmetropization process goes awry in some individuals resulting in common refractive errors like myopia. Research strongly suggests that optical defocus, in a manner similar to lens compensation, plays a role in this process. Yet, to date, treatment strategies for myopia that have manipulated the effective focus of the eye (e.g. bifocals and under-correction) have had only limited success in preventing myopia or slowing down the progression of myopia. Indeed, there is some evidence that seems to suggest that under-correction may induce myopia progression in some individuals. As we explain in the ensuing sections, these previous efforts to prevent myopia and myopic progression have assumed implicitly that eye growth is dominated by visual feedback associated with central vision and that vision-dependent mechanisms located in the center of the retina (i.e. the eye's fovea region) control refractive development.

The present invention is based on new findings and learning from experiments we have carried out that demonstrate that the peripheral retina is effective in modifying or controlling the development, progression and regression of myopia. Our findings demonstrated that image quality in the retinal periphery (i.e. peripheral vision, or vision associated with off-axis visual objects, and sometimes referred to as the "peripheral field") can play a major role in determining overall eye length and consequentially, stimuli from the peripheral field that promote peripheral eye growth will result in overall increases in eye size and myopia. The following observations from our experiments support the assertion that peripheral vision is effective and sufficient in controlling eye growth.

Observation 1—Axial myopia produced by peripheral form deprivation: Infant non-human primates were reared with annular diffuser lenses in front of both eyes that degraded peripheral vision without altering central vision. Specifically, 3-week-old rhesus monkeys were reared with annular diffuser lenses that had either 4 mm or 8 mm clear apertures that were centered in front of the pupils of each eye. When viewing through the apertures, a significant part of the central retina (approximately 22.5° and 45° with the 4 mm and 8 mm apertures respectively) received unobstructed clear retinal images. Due to the presence of the annular diffuser, the remaining peripheral regions of the retina were deprived of clear retinal images.

If eye growth is dominated solely by central vision, these annular diffuser lenses, which allow clear central vision, should have had little if any effect on refractive development. Yet, contrary to this conventional philosophy, the imposed peripheral form deprivation influenced central refractive development. The majority of treated monkeys developed significant myopic refractive errors that fell well outside the range of refractive errors for normal monkeys. These experimentally induced myopic errors were produced by an increase in vitreous chamber depth due to eye growth, which resulted in longer than normal eye axial lengths (i.e. axial elongation).

These results clearly demonstrate that alterations in the quality of peripheral retinal images are effective and sufficient to alter overall axial growth and refractive development.

Observation 2—Recovery from axial myopia does not require central vision: Infant monkeys exhibit a remarkable ability to recover from form-deprivation myopia. For example, in one experiment, we found that 18 out of 18 infant monkeys that had form-deprivation myopia (ranging from −1.0 D to −10.5 D) showed clear evidence of recovery from myopia when form deprivation was discontinued and the animals were allowed unrestricted vision.

Research in other species strongly suggests that this recovery is mediated by visual experience. In another experiment, we tested the hypothesis that peripheral vision is sufficient to drive this vision-dependent recovery. Five monkeys that had developed either myopia or hypermetropia as a result of wearing the annular diffuser lenses as described previously were tested. At approximately 4 months of age, the annular diffuser lenses were removed and a 2 mm to 3 mm circular section of the retina centered on the fovea of one eye (equivalent to approximately the central 5° to 7°) was ablated using an Argon photocoagulation (blue-green) laser. The other eye was not treated and the animals were subsequently allowed unrestricted vision.

If recovery from experimentally induced refractive errors were dependent on central vision, then the laser-treated eye should have failed to recover. It was found, however, that in all five monkeys, clear evidence for recovery in both the treated and untreated eyes was observed. Further and more importantly, there was no systematic difference in ocular growth and recovery in refractive errors between the ablated and unablated eyes.

These results convincingly demonstrate that central vision is not essential for the recovery from experimentally induced refractive errors and that peripheral vision is effective and sufficient to mediate normal emmetropization. More importantly, these findings spawn the idea leading to the present invention that peripheral vision could play a key role in the genesis of common refractive errors such as myopia and that manipulations of peripheral retinal images could predictably regulate eye growth and refractive development.

Additional studies have shown that interrupting myopia-inducing stimuli such as those of form deprivation or lens compensation, for even relatively short periods of time, reduces or even eliminates the myopia-inducing effects of such stimuli. The implication is that, a 'daily-wear' approach whereby the myope ceases to use a myopia-reduction device for certain periods during the day (e.g. removal after work and before sleep) may not be efficient and may well compromise its efficacy. Maximum efficacy is achieved when the myopia-reduction method and devices can be applied to the eye continuously through the day.

The present invention provides a method of retarding or eliminating the progression of myopia or preventing the initiation of the development of myopia in an individual by manipulating the off-axis, peripheral aberrations presented to an eye, in particular manipulating the relative curvature of field, thereby reducing or eliminating the peripheral retinal stimulus for eye axial elongation.

Further, for optimal and consistent control of off-axis, peripheral aberrations, the method must provide a device that consistently remains substantially coaxial (having substantial axial alignment or centration) with the optics of the eye.

Also further, for this method to be maximally effective, the predetermined refractive correction and off-axis, peripheral aberration control designs are preferably presented to the eye substantially continuously, to cover all open-eye situations.

The present invention also provides a method by which myopia development may be prevented, and myopia progression may be abated, retarded, and in many cases halted or reversed, with the use of novel optical devices and systems that retard or eliminate eye growth.

The methods and apparatuses of the present invention modify the progression of myopia by precisely controlling, in a predetermined fashion, the off-axis, peripheral aberrations and particularly the relative curvature of field of the corrective device, or the combined existing optical aberrations of the eye and the corrective device, such that the image of the peripheral visual field is shifted in a relative anterior direction ideally positioning the interval of Sturm partially or entirely in front of the peripheral retina while the central image is positioned at or near the fovea. This arrangement provides continuously clear central vision, and particularly, good visual acuity for the wearer while simultaneously retarding or eliminating the progression of myopia in myopes, or preventing the initiation of myopia in non-myopes (emmetropes or hypermetropes) with myopic tendencies (i.e. individuals with a predisposition to develop myopia) by providing a strong signal to reduce axial elongation in the periphery.

Since the devices of the present invention do not introduce any (central vision) defocusing effects, as are introduced by under-correction methods, or bifocal or progressive optical devices, such devices provide the wearer substantially simultaneously with a good quality visual acuity. Thus, the present invention offers the benefits of retarding progression of refractive error while simultaneously maintaining a substantially continuous, clear, useful visual image for the wearer.

While the aberration control aspect of the present invention may be implemented using any suitable optical devices including spectacles, contact lenses, corneal implants (e.g. on-lays or in-lays), anterior chamber lenses, intraocular lenses (IOL), etc., as well as by corneal or epithelial remodeling or sculpting methods including orthokeratology (a specialized contact lens technique which seeks to alter the refractive state of the eye by remodeling the cornea and epithelium by the short-term wearing of contact lenses of specific designs) and surgical refractive procedures (e.g. thermokeratoplasty, epikeratoplasty, LASIK, PRK, LASEK, etc.), the aberration control is preferably implemented in a device or method that can remain relatively centered to the axis of the eye such as an IOL, corneal implants, contact lenses, orthokeratology or refractive surgery. In this way, the precise control of peripheral aberration leading to the precise predetermined manipulation of the positions of peripheral and central field images can be maintained irrespective of eye movement.

The present invention is also preferably implemented in a spectacle, contact lens (soft or RGP or scleral haptic type), orthokeratology or corneal on-lay modality since changes in power and aberration profiles (required as the wearer's amount of myopia changes) can be readily made.

In the case of spectacles, contact lenses and orthokeratology, a new lens can be prescribed and dispensed readily.

For the on-lay, the epithelium is scraped away, the existing on-lay removed and a new on-lay affixed in place and the epithelium is allowed to re-grow over the device.

Further, the present invention is more preferably implemented in an extended wear or continuous wear contact lens modality or a corneal on-lay modality, thus providing a substantially continuous stimulus for maximizing efficacy of myopia retardation.

Typically, extended wear or continuous wear contact lenses, which may be soft, RGP or scleral/haptic, have sufficient oxygen permeability and other properties to permit the lens to be left in the eye during sleep and still receive sufficient oxygen from the tarsal conjunctiva to maintain ocular health despite atmospheric oxygen not being available due to the closed eye-lid.

For orthokeratology, the contact lens (which may also be of the high oxygen permeability kind suitable for extended or overnight wear) is worn for a short period (e.g. during sleeping hours) to remodel the epithelium and cornea after which the contact lens is removed leaving the patient in the desired refractive and aberration state according to the present invention without contact lens wear for the period of effectiveness of the orthokeratology. The contact lens design for use in the orthokeratology modality has a dual role. Thus, the contact lens is designed such that when worn on eye during the 'treatment' or remodeling period, the combined eye, tear-lens (created by the filling of tears between the back surface of the contact lens and the front surface of the corneal epithelium) and contact lens aberrations are manipulated according to the present invention. In addition, the contact lens back or posterior surface profile, together with its rigidity and thickness profile, all of which controls the remodeling of the epithelium and cornea, can be designed and selected so that upon lens removal (after the lens wearing 'treatment' period of orthokeratology), the remodeled cornea and epithelial profile is such that the residual ocular aberrations is manipulated according to the present invention.

The development leading to the methods and devices of the present invention is now discussed in detail.

FIG. 1a illustrates an ideal optical system. The optical system [10] is refracting light from an object [20], denoted by arrow along object points C, A and B, to be focused to the image [30] with image points C', A' and B'. In an ideal optical system, the focused image lies precisely along the image-receiving surface [40]. Typically, for conventional optical systems, the image-receiving surface [40] is a flat or planar surface. Hence the ideal focused image should also be flat or planar. That is, points C', A' and B' on the focused image [30] should lie on the image-receiving surface [40]. When the focused image [30] is in close alignment with the image-receiving surface [40], then every imaged point (e.g. C', A', B') will be focused sharply onto the image-receiving surface [40] and the image is clear along its entirety.

Figure 1B:
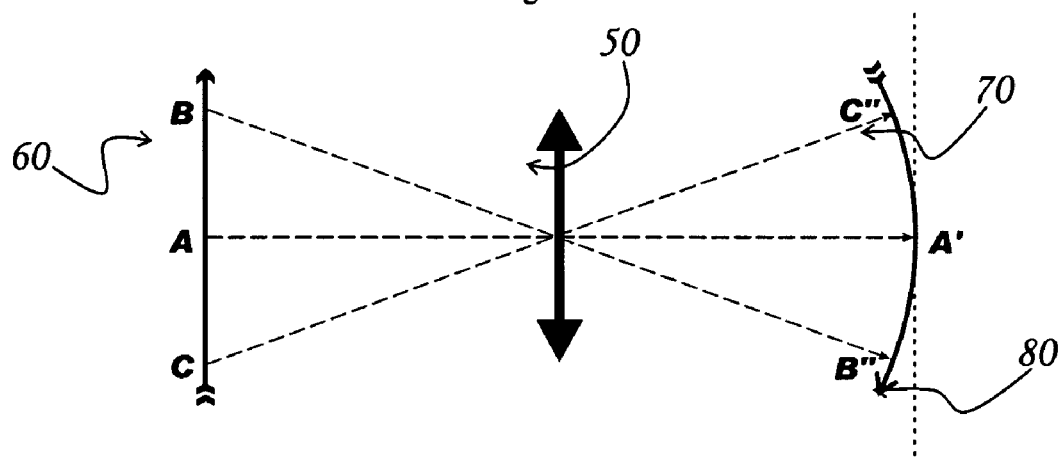

Many optical systems suffer an off-axis aberration known as "curvature of field". In FIG. 1b, another optical system [50] is refracting light from an object [60] to an image [70]. However, due to the presence of curvature of field, the focused image [70] does not lie fully aligned to the flat image-receiving surface [80]. In this example, light from on-axis (i.e. lying on or along the optical axis of the optical system) object point A is focused onto on-axis image point A' on the image-receiving surface [80] and will therefore appear sharply focused. However, light from off-axis (i.e. lying away from or at an angle to the optical axis of the optical system) object points C and B is focused to off-axis image points C'' and B'' that lie in front (i.e. in the direction against the direction of light coming from the object) of the image-receiving surface [80]. These image points C'' and B'' will therefore be out of focus and appear blurred. In optical systems which possesses curvature of field, such as in this example, in which the off-axis peripheral image points are positioned substantially more anteriorly or in front of (i.e. in a direction against the direction of light, which travels from object to image) the central, on-axis image point, the system may be said to have a negative curvature of field.

Figure 1C:
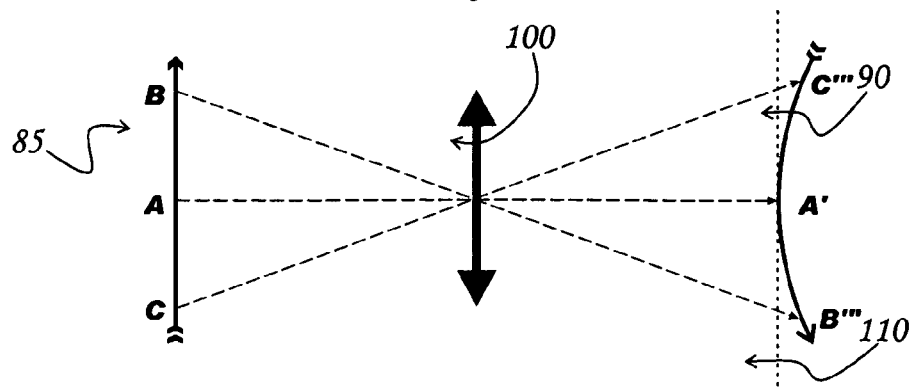

FIG. 1c illustrates an optical system with positive curvature of field. In such a system, the image [90] of the object [85] created by the optical system [100] is not aligned with the flat image-receiving surface [110]. While the central on-axis image point A''' focused from central object point A lies on the image-receiving surface [110], the off-axis peripheral object points C and B are focused to off-axis peripheral image points C''' and B''' which lie substantially behind the image-receiving surface [110] and relatively more posteriorly, or behind (i.e. in the direction of light) the central, on-axis image point A'''. Here, image point A''' will appear sharply focused while image points C''' and B''' will be out of focus and appear blurred.

It should be noted that in the quantitative description of optical aberrations, a number of different sign conventions have been used by various people. In this document, we adopt the sign convention whereby distances are measured from a reference position to the point of interest, and are positive if the direction of that measurement is the same as the direction of travel of light through the system and negative when measured in a direction against the direction of light. For curvature of field, the reference surface is the ideal (unaberrated) image surface and the point of interest is the aberrated curved image surface. Thus, for FIG. 1b, the curvature of field is measured as the distance from the unaberrated planar image surface [80] to the curved aberrated surface [70]. And since the direction of this measurement is against the direction of travel of light through this optical system (which is left to right), the curvature of field is negative.

Conversely, for FIG. 1c, the curved image surface [90] as measured from the ideal reference surface [110] is in the direction of light travel and hence the curvature of field is positive.

Figure 2A:
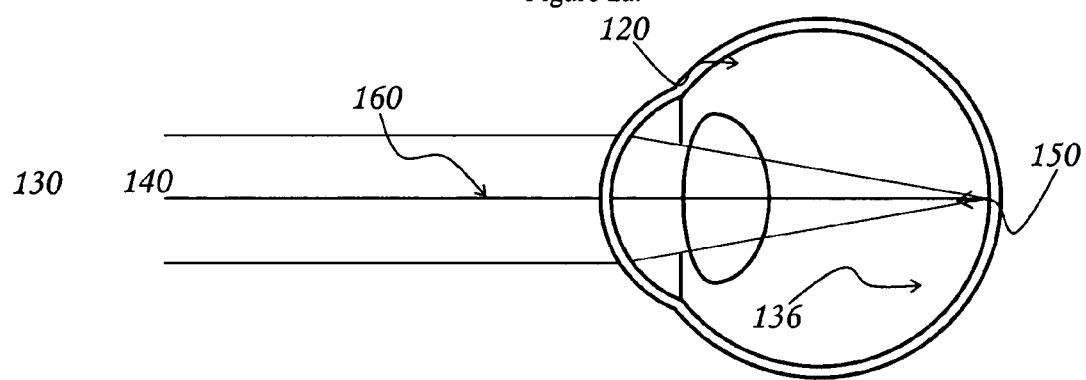
FIGS. 2a to 2h are optical diagrams of the eye and relative field curvature graphs explaining relative curvature of field for the eye and its various types.
Figure 2B:
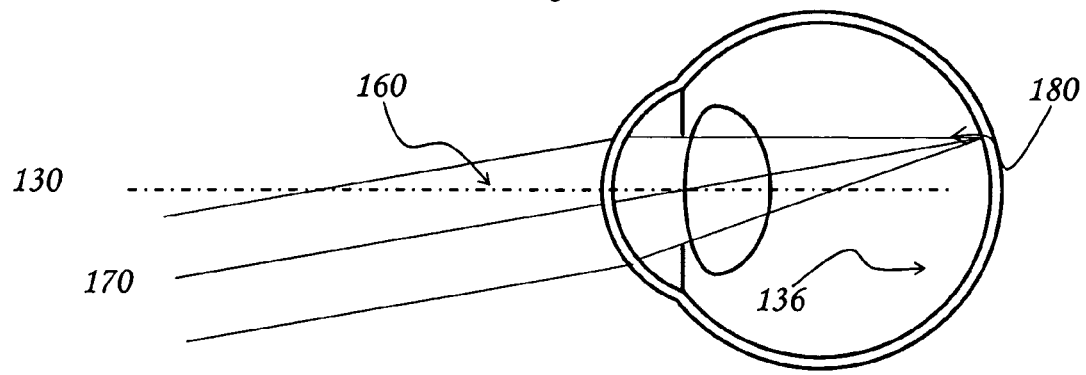
Figure 2C:
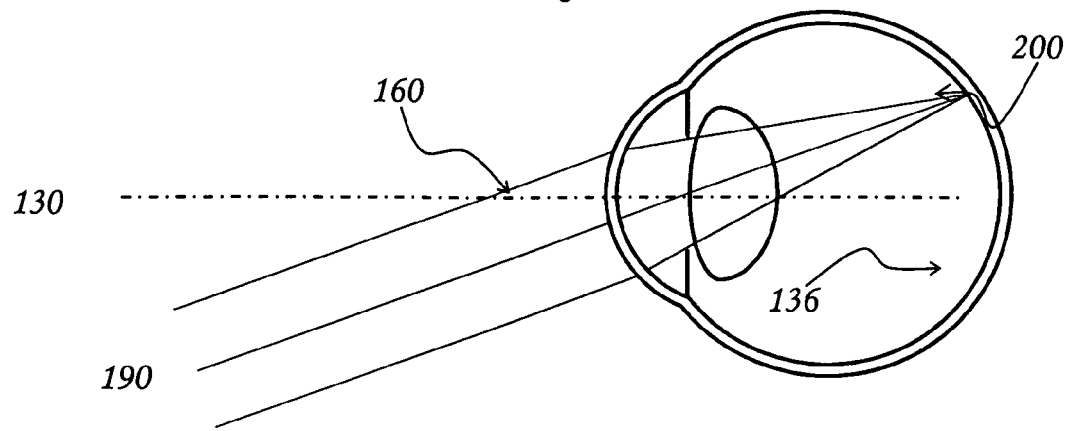

Unlike most optical systems, the image-receiving surface of the eye, which is the retina, is not a flat or planar surface. Therefore, in order to acquire sharply focused image points, the image surface would need to be curved in a concomitant manner to the retinal surface. In FIGS. 2a to 2c, an eye [120] is receiving light from a distant scene [130] from three different object directions [140, 170 and 190]. These directions are often called "field angles". The image-receiving surface, i.e. the retina of the eye [136] is also shown. The object [140] point and image [150] point from the part of the scenery which lie substantially on the optical axis [160] equates to the zero field angle and are called the "central" or "on-axis" objects and images respectively. This is illustrated in FIG. 2a.

As object and image points are located progressively further from the optical axis and the central object and image points, the field angle is said to increase. Such object and image points are called "peripheral" or "off-axis" objects [170] and images [180] and have finite (non-zero) field angles. This is illustrated in FIG. 2b. FIG. 2c shows peripheral or off-axis object [190] and image [200] points at large field angles.

Figure 2D:
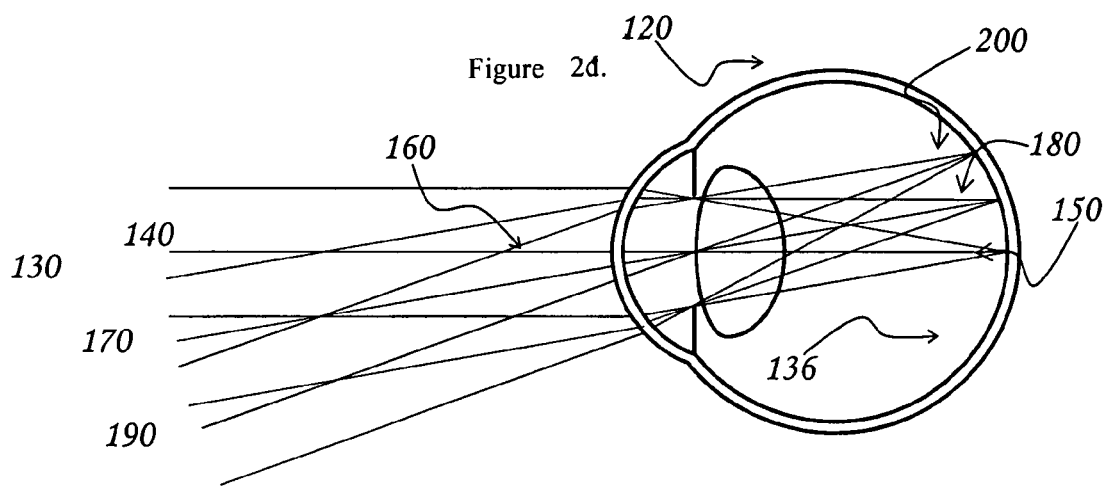

In order for the eye to receive sharply focused image points across the entirety of the image, image points [150, 180 and 200] from all field angles must lie precisely on the retina surface [136] at the same time. This ideal scenario is illustrated in FIG. 2d.

Since the retina of the eye is not a flat surface, when considering the curvature of field of the optics of the eye, it is more convenient to consider the relative curvature of field. The relative curvature of field can be defined as the axial (antero-posterior, or forward-backward) position of the image points at different field angles relative to the central image point and to the retina. Thus, even though the image surface [136] of the eye [120] illustrated in FIG. 2d has an actual negative curvature of field since the peripheral image points [180 and 200] are positioned more anteriorly than the axial image point [150], there is no net relative curvature of field (i.e. relative to the curvature of the retina [136]) and hence image points at all field angles are sharply in focus on the retina and the entirety of the image is seen clearly.

Figure 2E:
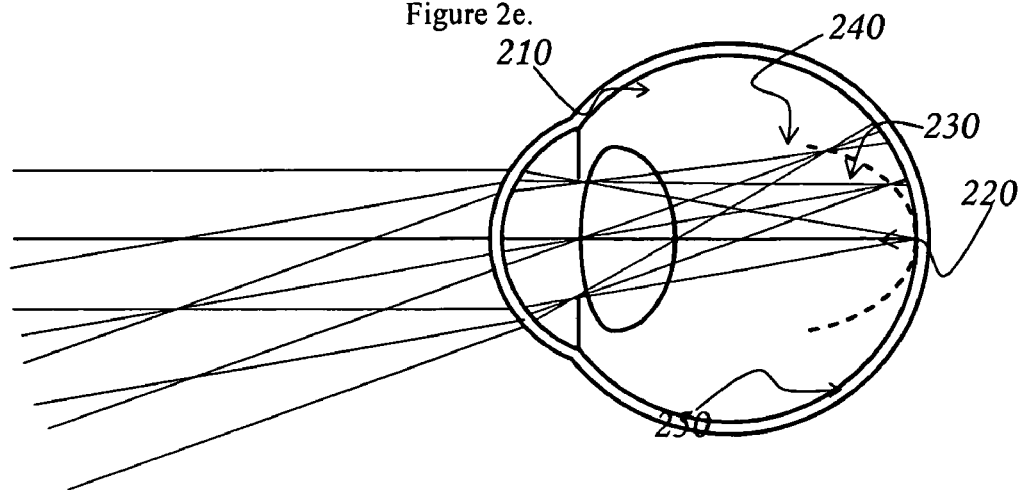

FIG. 2e shows an eye [210] that has substantial amount of negative curvature of field. Light from a distant scenery (object) is focused by this eye in such a way that while the on-axis central image point [220] is focused on the retina, image points for the intermediate [230] and far [240] peripheral (off-axis) field angles are focused progressively more anteriorly, (in front of, or in the direction against the direction of light) than the central image point [220]. Since the image points [230 and 240] at these peripheral field angles are also focused substantially in front of the curved retina [250], the image points [230 and 240] of the peripheral fields will be out of focus on the retina and appear blurred to the eye [210]. Therefore, this eye suffers from negative relative curvature of field.

Figure 2F:
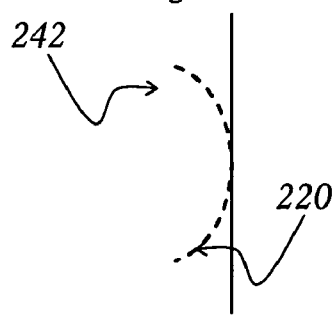

For graphical representations and ease of evaluation of relative curvature of field conditions, it is more convenient to plot relative curvature of field by 'mapping' the curved retinal surface onto a flat surface. That is, the curvature of the retina is flattened geometrically and thus can be subsequently represented by a straight line or flat surface. The straight-line representation is the two-dimensional cross-section of the three-dimensional geometrically flattened (or remapped) plane retinal surface. FIG. 2f shows such a graph of the relative curvature of field of the eye illustrated in FIG. 2e. The retina has been remapped to a straight line [220]. This provides an immediate indication that the image surface [242] is situated in front of the retina [220] across its entire extent. For the remainder of this document, this type of graphical representation of relative curvature of field, which is also frequently used in the output of computer-assisted optical modeling programs, will be called a "relative field curvature graph". Since the entire performance in terms of relative curvature of field of the optical system or eye is summarized and readily evaluated in a relative field curvature graph, the remainder of the details concerning the optical system or eye that produced the curvature of field outcome need not be included in such a graphical representation (as has been done in previous figures).

Figure 2G:
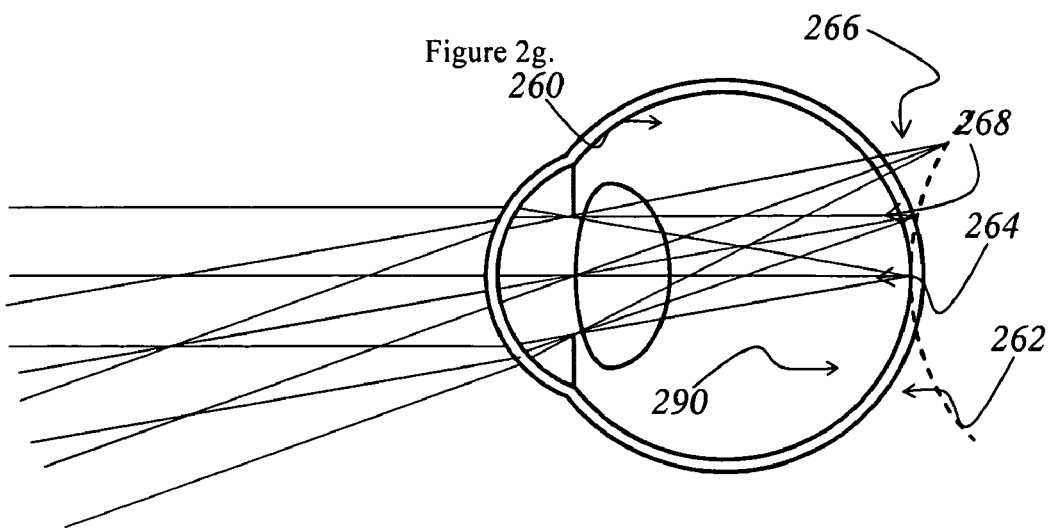
Figure 2H:
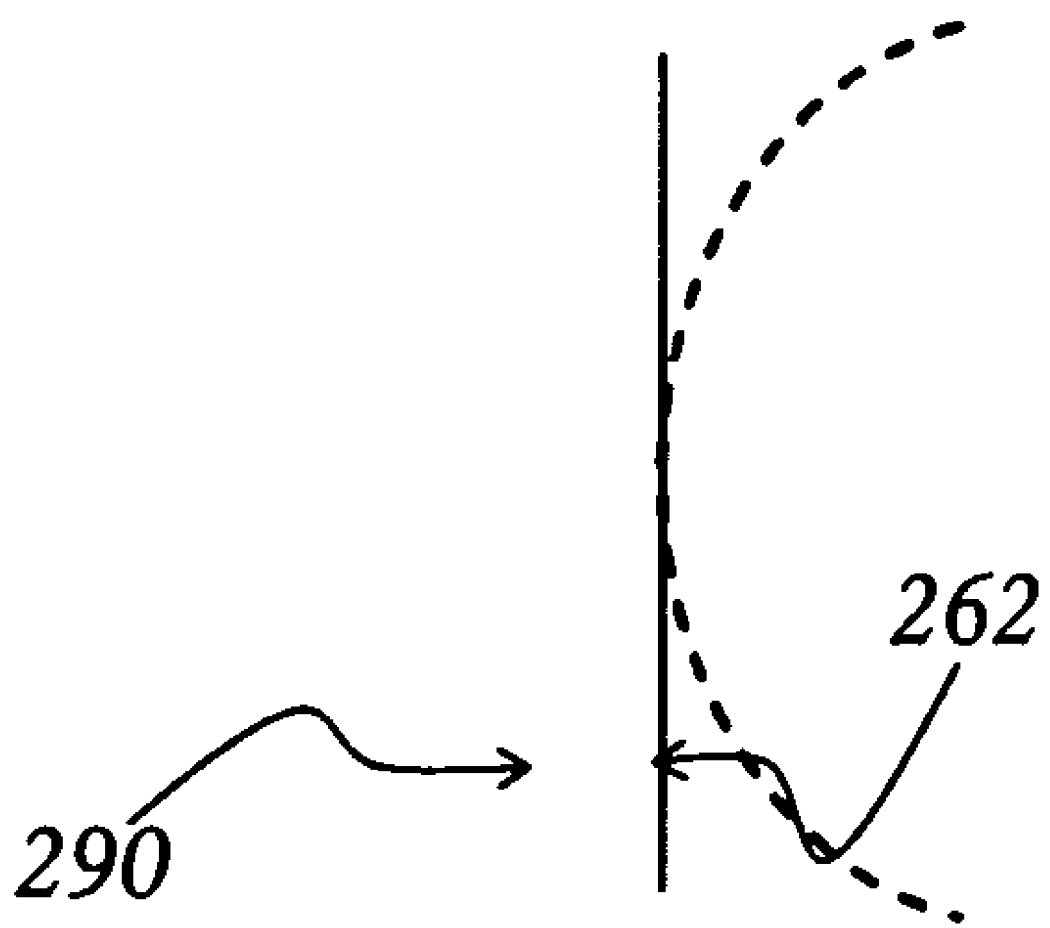

FIGS. 2g and 2h illustrate an eye [260] with positive curvature of field. As seen in the relative field curvature graph in FIG. 2h, this eye also has positive relative curvature of field in which the image surface [262] is such that the off-axis, peripheral field angle image points [266 and 268] are located more posteriorly (or behind, i.e. in the direction of the light) than the central on-axis image point [264] and the retina [290]. In this case, the central image point [264] is sharply focused while the peripheral field image points [266 and 268] are not in focus and will appear blurred.

Figure 3A:
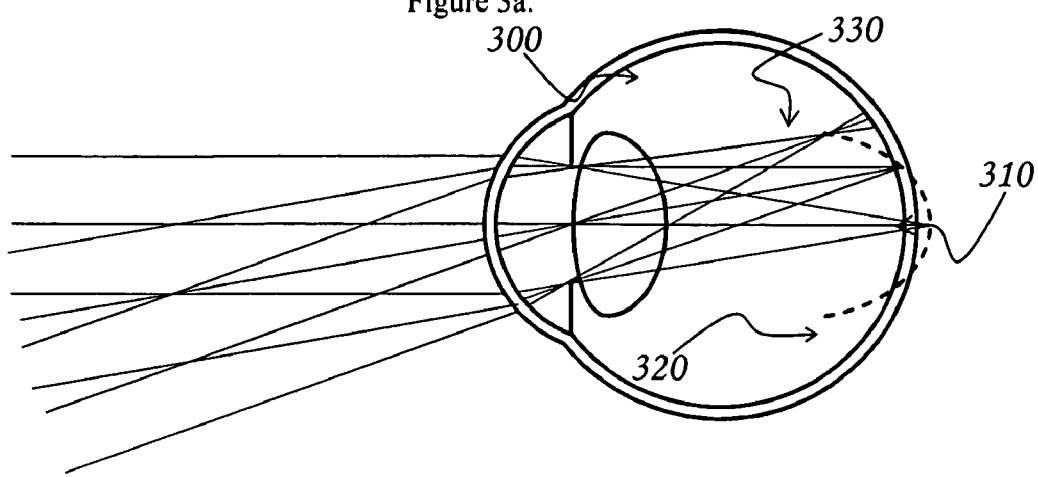
FIGS. 3a to 3d are optical diagrams of the eye and relative field curvature graphs explaining how relative curvature of field can render a myopic eye relatively locally hypermetropic in the peripheral field and a hypermetropic eye relatively locally myopic in the peripheral field.
Figure 3B:
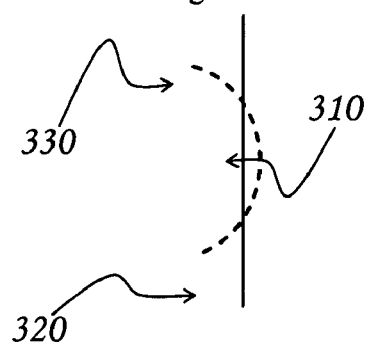

FIGS. 3a and 3b illustrate an eye [300] that has a negative curvature of field. Since the central on-axis image point [310] is located behind (i.e. in the direction of light) the retina [320], this eye is considered hypermetropic as measured using standard techniques such as auto-refractors, refractor-heads or trial frames, in the manner that eye-care practitioners such as ophthalmologists, optometrists, opticians, orthoptists and vision scientists are familiar. However, due to the negative curvature of field present in this example, the off-axis peripheral image points [330] for large field angles are located in front of (i.e. in the direction opposite to the direction of light) the retina [320]. Thus the eye of this example is actually relatively myopic for the peripheral visual field. This is best seen in the relative field curvature graph of FIG. 3b, which clearly shows that the central [310] to mid-peripheral field is hypermetropic (focus behind retina) but the mid-peripheral to far-peripheral [330] field is myopic (focus in front of retina).

Figure 3C:
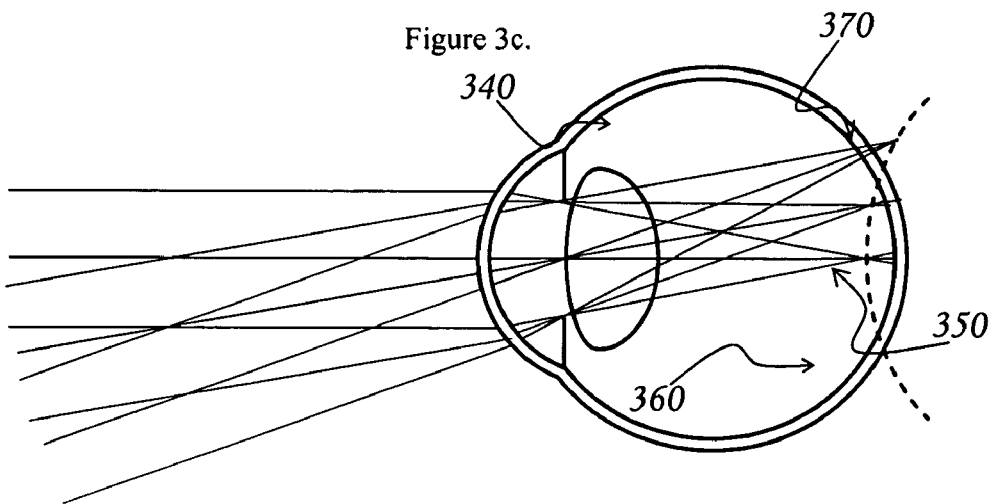
Figure 3D:
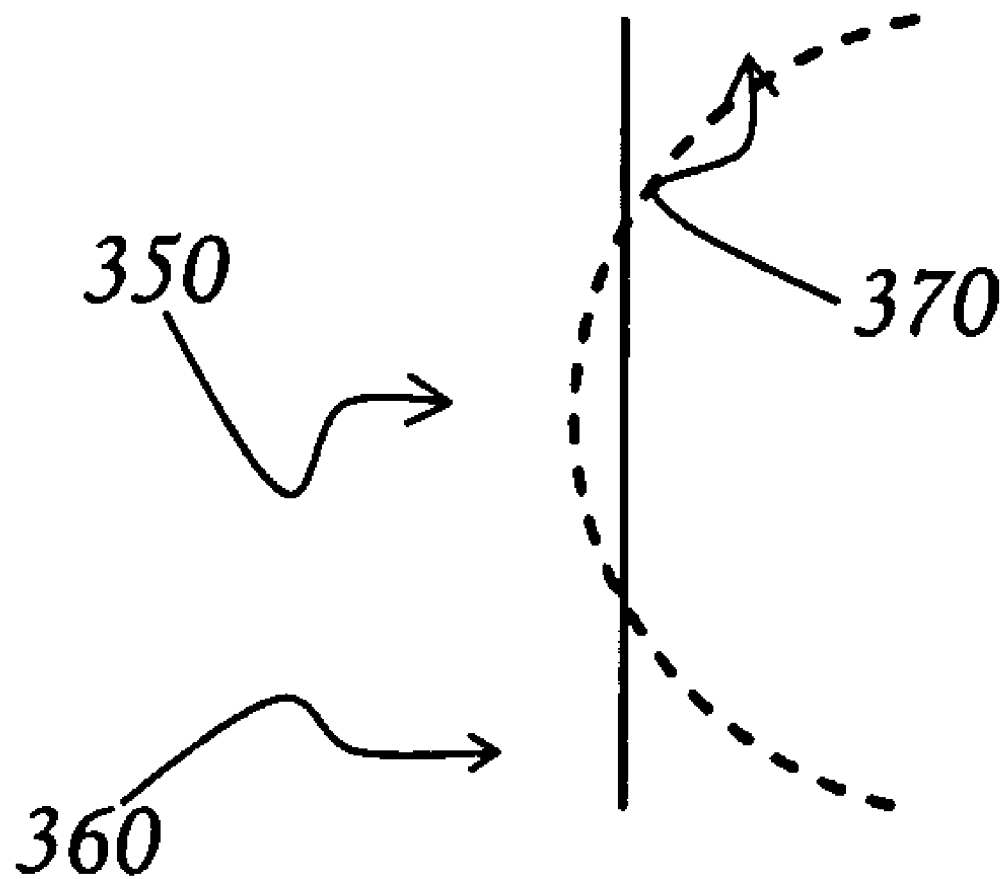

FIGS. 3c and 3d illustrate an eye [340] that has a positive curvature of field. Since the central on-axis image point [350] is located in front of (i.e. opposite to the direction of light) the retina [360], this eye is considered myopic when measured using standard techniques such as auto-refractors, refractor-heads or trial frames, in the manner that eye-care practitioners are familiar. However, due to the positive curvature of field present in this example, the off-axis peripheral image points [370] for large field angles are located behind (i.e. in the direction of light) the retina [360]. Thus the eye of this example is relatively hypermetropic for the peripheral visual field. This is best seen in the relative field curvature graph of FIG. 3d, which clearly shows that the central [350] to mid-peripheral field is myopic (focus in front of retina) but the mid-peripheral to far-peripheral [370] field is hypermetropic (focus behind retina).

FIGS. 4a through 4k detail the rationale to the present invention. All attempts so far at inducing or controlling myopia growth implicitly consider only the refractive state of the central field. This is because the current standard for measurement of refractive error, which includes use of trial frames, refractor-heads and auto-refractors by ophthalmologists, optometrists, opticians or other eye-care practitioners, all measure the refractive state of the eye at or very near the fovea, which is situated substantially at the central field of the eye. Within this conventional understanding, as shown in the schematic eye and optics in FIG. 4a, a negative refractive powered blur, i.e. by placing the image point [402] behind (i.e. in the direction that light travels through the eye) the retina [404] and fovea [406], either due to the inherent optics of the eye [408] or by deliberate intervention such as the prescribing of excessive negative power in a spectacle lens [410], would provide a stimulus for axial elongation (as indicated by the direction of the arrow [412]) which leads to growth of the eye [414] towards the posteriorly located image points in accordance with the phenomenon of lens compensation myopia, and consequently either induces myopia in an emmetrope (a person without any refractive error) or hypermetrope, or causes the further progression of myopia in a myope.

This confined consideration of only the on-axis or central field refractive state of the eye forms the basis of conventional optical approaches adopted in attempts to prevent the onset or retard the progression of myopia. One such conventional approach is to use a positive powered blur, one that places the implicitly central or on-axis image in front of the fovea to remove the stimulus for axial elongation and eye growth. This subsequently leads to the conventional approach of retarding the progression of myopia by the use of under-correction for myopia. As illustrated in the schematic eye and optics of FIG. 4b, under-correction involves the deliberate focusing of the central on-axis image [416] to in front of the retina [418] and fovea [420]. This is achieved by prescribing a slightly more positive power (or slightly less negative power for myopes—hence the commonly used term "under-correction" to describe this approach) to an optical correction [422] than that normally prescribed for the individual to achieve clear vision. For example, a myope requiring a −4.00 D lens for clear vision may be prescribed a −3.50 D lens. While this approach is somewhat effective in retarding myopia progression in some individuals, it has been shown not to be effective in all individuals. Indeed, there are research results that suggest that under-correction may actually increase myopia in some individuals. Further, and most problematically, this approach explicitly blurs the image at the fovea [420] giving the lens wearer less than optimum vision and visual acuity, and may prevent the wearer from being able to conduct certain critical visual tasks, e.g. driving.

We have now shown in our experiments that the peripheral field alone is effective and sufficient in driving eye growth, which leads to axial elongation and ultimately myopia development or progression.

Figure 4A:
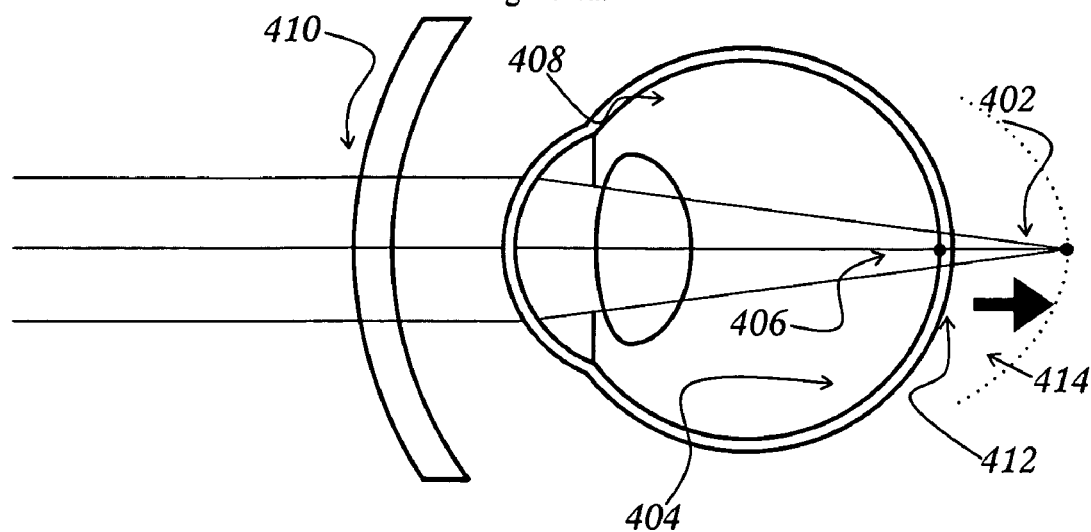
FIGS. 4a to 4l are optical diagrams of the eye, graphs of experiment results and relative field curvature graphs detailing the principle of the present invention.
Figure 4B:
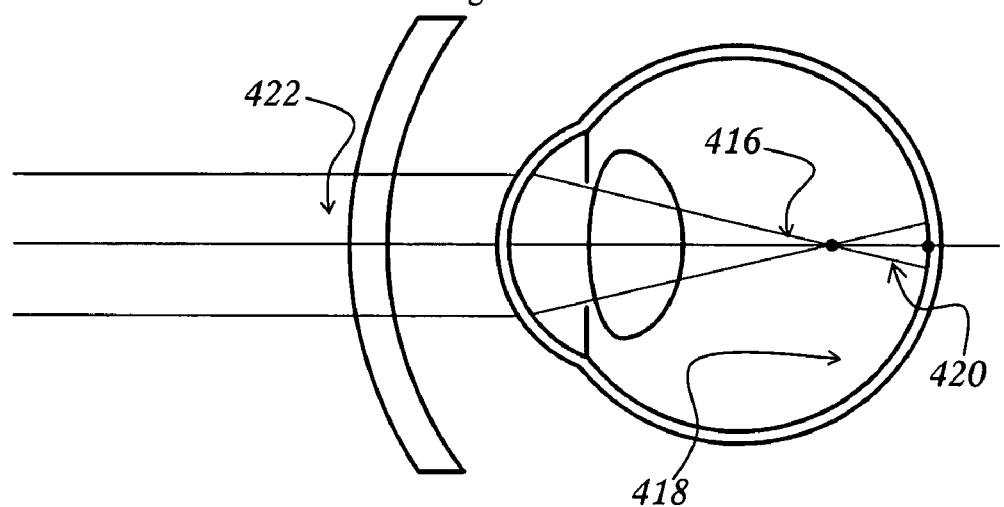
Figure 4C:
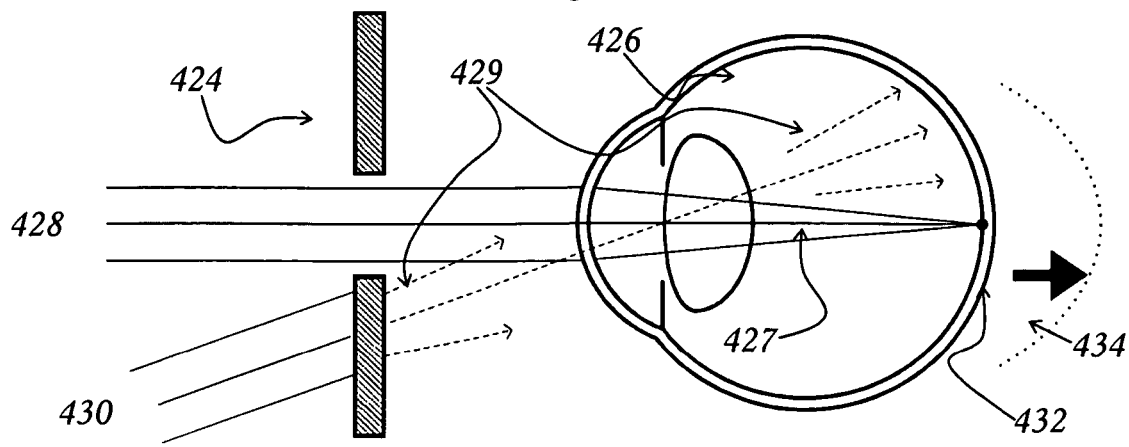
Figure 4D:
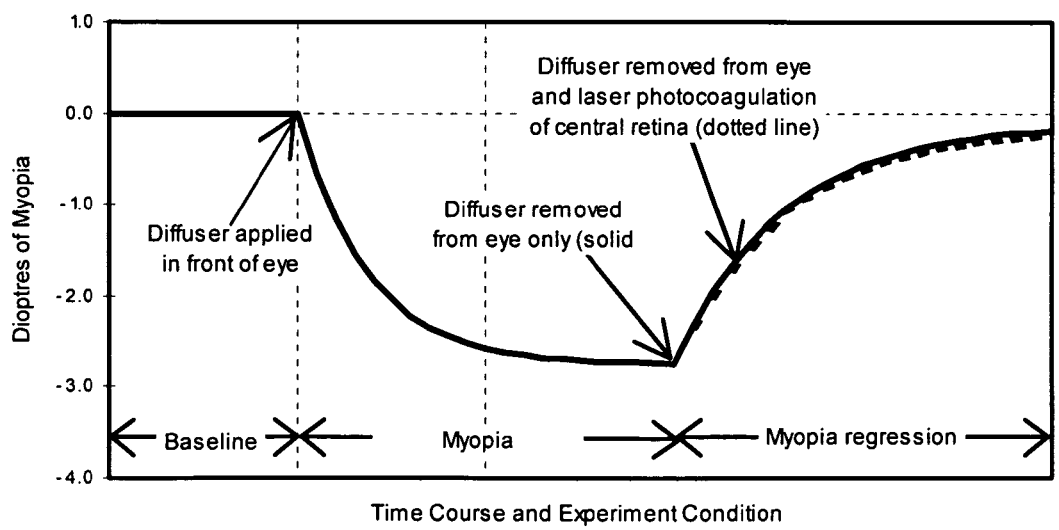

The outcome of one key experiment is illustrated in the schematic eye and optics of FIG. 4c. In this experiment, primates were reared with annular diffusing lenses [424] placed in front of the eye [426]. The diffusing lens [424] allows light rays [427] from on-axis, central field objects [428] to reach the eye [426] unobstructed. The same annular diffuser [424] scatters or diffuses light rays [429] from off-axis, peripheral field objects [430]. This scattering induces form deprivation only to off-axis visual objects in the peripheral field [430], while maintaining clear vision for the central field [428]. It is known to vision scientist working on myopia development that form deprivation applied to the entire visual field (or central field) of the eye induces axial growth leading to myopia. In our experiment, involving form deprivation to only the peripheral field, the eye also developed myopia due to axial elongation (indicated by the direction of the arrow [432]) and eye growth [434].

In an extension to the experiment, the annular diffusing lenses [424] were removed from some eyes following development of substantial amounts of myopia. When the diffusers were removed, the amount of myopia in the primates decreased as illustrated by the solid line in the graph of FIG. 4d.

Further, in a parallel extension to the experiment, for other eyes, in addition to removal of the diffusers following development of substantial amounts of myopia, central vision of the primate's eye was eliminated, by using an Argon (blue-green) laser to ablate the macular portion of the retina by photocoagulation, essentially blinding central vision while sparing peripheral vision. Even when on-axis central, foveal vision was interrupted in this manner, the decrease in myopia remained similar to when central vision was not disrupted as illustrated by the broken line in the graph of FIG. 4d.

EXAMPLES

The following additional experiments represent further investigations conducted to address a series of questions related to the relative importance of the fovea versus the peripheral retina in regulating vision-dependent changes in eye growth and the question of whether or not the peripheral retina is sensitive to optical defocus. All experiments were carried out on the live rhesus monkey as this species is considered to be one of the most valid models for refractive error development in human.

The results from the following Examples support the present discovery that the periphery plays a major role in: 1) the regulation of eye growth; 2) the development of myopia; 3) the impact of peripheral vision (peripheral vision is demonstrated to overshadow the influence of central vision); and that 4) manipulations of peripheral vision influences eye growth.

Example 1

Example 1 describes an experiment addressing the question of whether the fovea is essential for normal emmetropization (i.e. normal eye growth and refractive development).

The fovea and most of the peri-fovea (i.e. the region of the retina immediately surrounding the fovea) were ablated using either an argon laser or a frequency-doubled YAG laser in one eye of five infant monkeys (average age 19 days). While a YAG laser was used, it is understood that any laser able to achieve the requisite level of ablation could have been used in this or subsequent Examples where a laser was used. The monkeys were subsequently allowed unrestricted visual experience. Refractive development was monitored for over one year in three animals and for over 200 days in the other two monkeys (i.e. through the key periods of the normal emmetropization process for young monkeys).

Figure 13A:
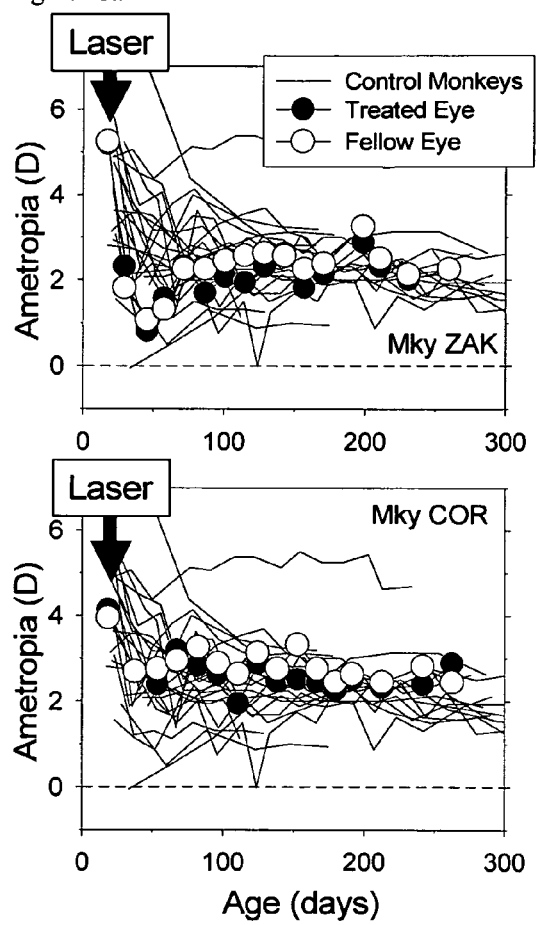
FIGS. 13a to 13d illustrate the results of procedures performed upon intact foveas and peri-foveal retinas according to the procedures outlined in Example 1.
Figure 13B:
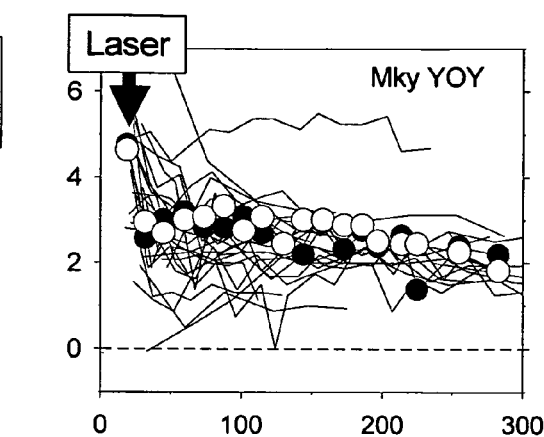
Figure 13C:
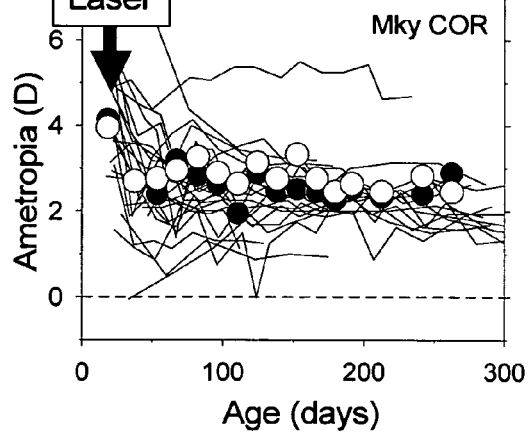
Figure 13D:
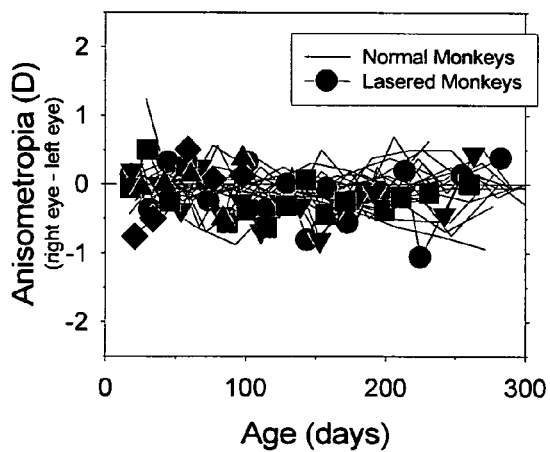

One would have expected differences in the rate and/or effectiveness of the emmetropization process between the treated and non-treated eyes, if the fovea played a significant role in refractive development. However, there were no differences between eyes in refractive error and/or axial dimensions at any time throughout the observation period. The two (treated and non-treated) eyes of a given animal were always well matched. See FIGS. 13a to 13c, which show refractive error data for both eyes of the three animals (experiment code ZAK, YOY, COR) that were followed the longest. FIG. 13d shows the inter-ocular differences in refractive error for all five treated animals. In FIG. 13d, the results for each individual animal is denoted by a different black symbol—square, circle, diamond, triangle and inverted triangle. For comparison, black lines without symbols represent normal control data.

The results from this experiment demonstrate that a functioning fovea is not essential for normal emmetropization (i.e. control of normal eye growth and refractive state). The peripheral retina, by itself, can regulate normal refractive development.

Example 2

This experiment addressed the question of whether an intact fovea is essential for the development of form deprivation myopia, and whether the periphery in isolation can produce abnormal ocular growth in response to a myopia-genic stimulus. At about three weeks of age, the fovea and most of the peri-fovea in one eye of nine infant monkeys were ablated using an argon laser. Subsequently, monocular form deprivation was induced in the laser-ablated eye using a diffuser spectacle lens.

Figure 14A:
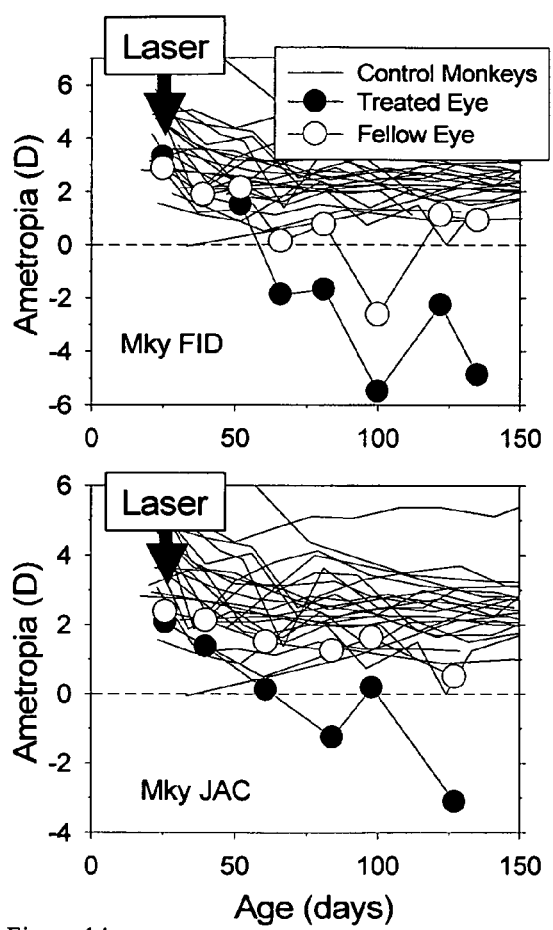
FIGS. 14a to 14d illustrate the results of procedures performed upon intact foveas and peri-foveal retinas according to the procedures outlined in Example 2.
Figure 14B:
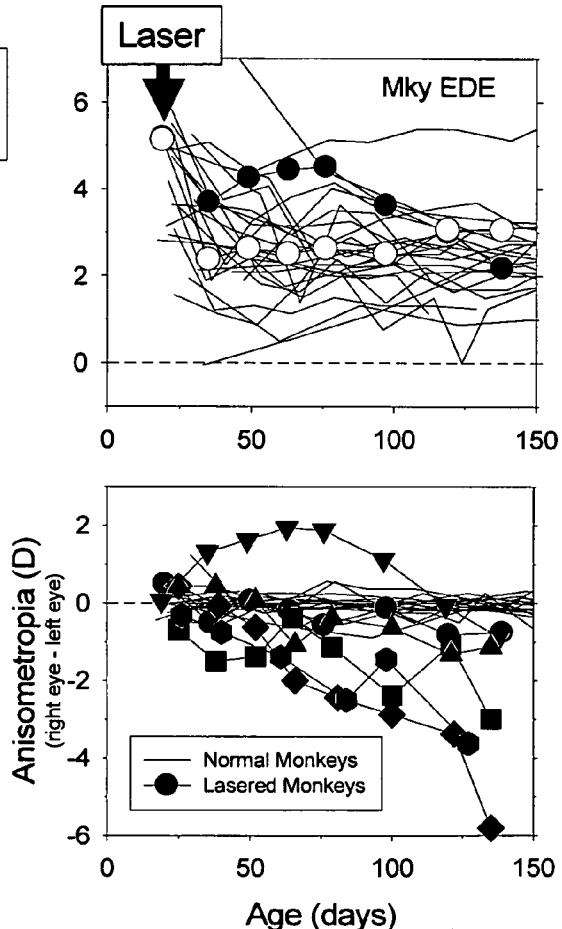
Figure 14C:
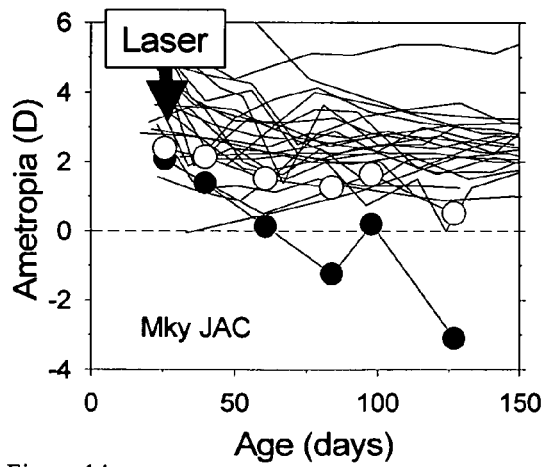
Figure 14D:
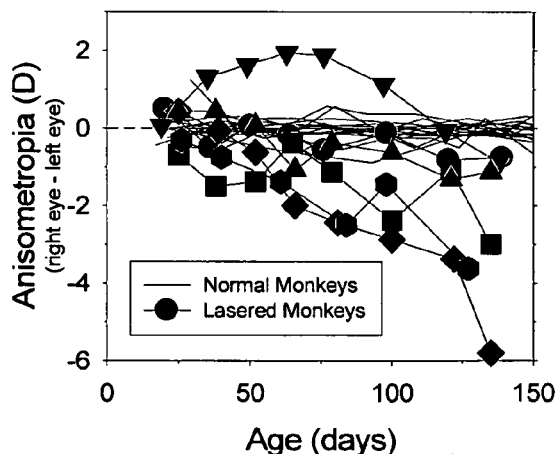

For all of the six monkeys that completed the rearing period (basically from three weeks to five months of age), the treated (i.e. laser-ablated and form deprived) eyes became longer and more myopic than their fellow eyes. FIGS. 14a to 14c show representative refractive error data for three animals (experiment code FID, EDE, JAC). FIG. 14d shows the difference between eyes for all six monkeys. In FIG. 14d, the results for each individual animal is denoted by a different black symbol—square, circle, diamond, triangle, inverted triangle and hexagon. For comparison, black lines without symbols represent normal control data.

The results of this experiment demonstrate that a functioning fovea is not essential for the development of form deprivation myopia and that chronic image degradation in the periphery can produce axial myopia at the fovea.

Example 3

This experiment considered whether an intact periphery is essential for normal emmetropization.

In nine monkeys, at about three weeks of age, the mid- to far-peripheral retina of one eye was ablated with a frequency-doubled YAG laser. For six of these treated monkeys, the ablations extended from about the temporal vascular arcades, all the way to the ora serrata (i.e. the most peripheral limit of the retina). For the other three monkeys, the ablations extended from the vascular arcades to the equator. Subsequently all of these animals were allowed unrestricted vision.

Many of the animals showed initial hyperopic shifts in refractive error (sometimes quite significant) but almost all animals developed balanced refractive errors shortly after the laser procedure (i.e. both eyes ended up with the same refractive error despite big differences between eyes in lens dimensions and axial length). However, in every case the treated eyes eventually started to drift in the hyperopic direction. FIGS. 15a to 15c show representative refractive error data for three animals (experiment code CAS, YOK, CUT). FIG. 15d shows the difference between eyes for all monkeys. For comparison, black lines without symbols represent normal control data. In FIG. 15d, the results for each individual animal that has been treated with ablation of the peripheral retina is denoted by black symbols—square, circle, diamond, triangle and inverted triangle; while the results for individual animal that has been treated with ablation of the fovea is denoted by white (open) circles. The results for this group are more complicated to interpret because the laser procedures produce a number of direct effects on the eye in both groups. For example, the anterior segment of the eye was affected so that the crystalline lens appeared to be positively accommodated (a decrease in anterior chamber depth, an increase in lens thickness and a decrease in radii of curvature for the front and back lens surfaces) and there was a decrease in vitreous chamber depth.

The results indicate that peripheral laser ablations alter normal refractive development. Moreover, the results demonstrate that the remaining central retina was not sufficient to maintain the normal refractive error balance between the two eyes over a long period of time.

Example 4

This experiment addresses whether an intact peripheral retina is essential for form deprivation myopia.

In two monkeys, at about 3 weeks of age, the mid- to far-peripheral retina of one eye was ablated with a frequency-doubled YAG laser. The ablations stopped at the equator. Subsequently, monocular form deprivation was produced in the laser-ablated eyes using a diffuser spectacle lens.

Figures 16A, 16B:
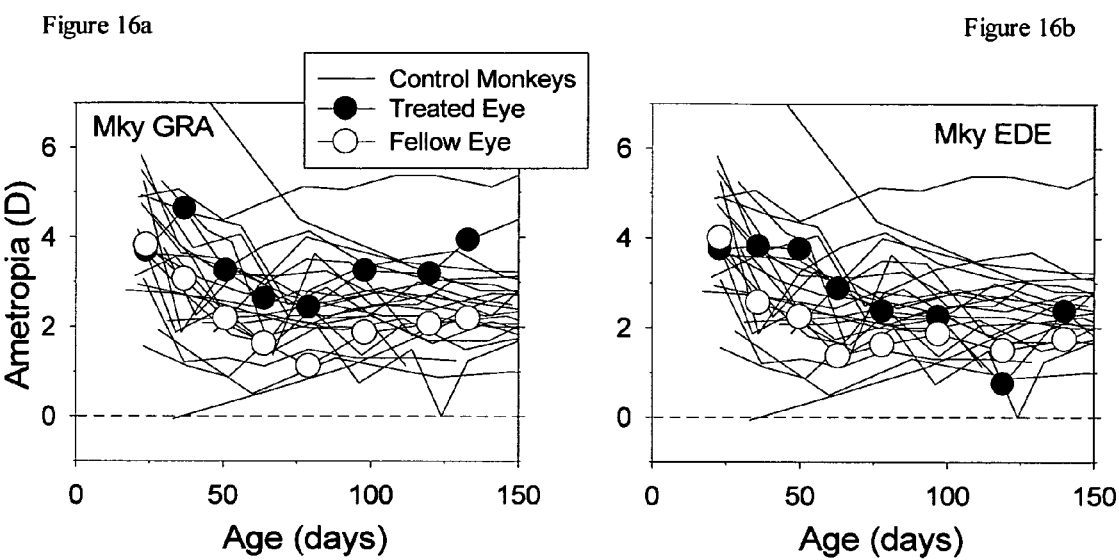
FIGS. 16a and 16b illustrate the results of procedures performed upon the mid- to far-peripheral retinas according to the procedures outlined in Example 4.

As illustrated in FIGS. 16a and 16b, neither of the two monkeys showed any signs of form deprivation myopia in their treated eyes. (For comparison, black lines without symbols represent normal control data.) The results demonstrate that peripheral vision may be essential for abnormal axial growth produced by a myopia-genic stimulus.

Example 5

This experiment addressed whether peripheral defocus can alter refractive development at the fovea. This experiment is the defocus analogue to the peripheral form deprivation experiments described in Examples 3 and 4 above.

Beginning at 3 weeks of age, infant monkeys were fitted with binocular negative-powered (seven animals wore −3 D) or positive-powered (four monkeys wore +3 D) spectacle lenses in front of both eyes. A 6-mm diameter aperture was cut in the center of the lenses over the pupils of both eyes so that central vision was potential unrestricted. In this way, we introduced selective hyperopic (relatively negative, where the image is located behind the retina) or myopic (relatively positive, where the image is located in front of the retina) defocus in the periphery.

For the negative-lens group, five of the seven monkeys showed clear signs of myopic refractive development. This demonstrates that peripheral hyperopic defocus (where the image is located behind the retina) produced axial myopia. See FIGS. 17a to 17d.

This is shown in FIGS. 17a to 17d in which white symbols represent left eye refractive error and black symbols represent right eye refractive error versus. Results for animals that wore negative-powered lenses with 6 mm apertures are shown in FIGS. 17a and 17c while results for animals that wore positive-powered lenses with 6 mm apertures are shown in FIGS. 17b and 17d. Thin solid lines without symbols represent normal control monkeys for comparison.

The results shown in FIGS. 17a to 17d demonstrate that relative myopic defocus (with the image in front of the retina, or less hyperopic defocus) in the periphery does not interfere with normal refractive development at the fovea.

Some data suggest that the positive periphery lenses altered the shape of the eye. The results of the experiments conducted in Examples 1-5 show that peripheral defocus can alter foveal refractive development and that imposed relative hyperopic and myopic peripheral refractive errors differentially alter ocular growth.

The foregoing examples and experimental results demonstrate clearly that appropriate myopia-reducing stimuli in only the peripheral field (in essence localized stimulation of only the periphery) are effective and sufficient to retard or prevent the development or reduce, eliminate or reverse the progression of myopia. While the earlier experiments (Examples 1 to 4) addressed mainly form-deprivation myopia, we postulated that the link between form-deprivation and lens compensation myopia in general would mean that localized lens compensation effects (i.e. applied only to the peripheral retina—in essence, under-correction applied only to the peripheral field) would also provide similar stimuli for myopia reduction. This was strongly supported by the results of Example 5 which showed that optical intervention to only the periphery of the retina produces myopia development responses analogous to lens compensation. That is, defocus at only the peripheral retina is sufficient for control of myopia development.

Under-correction of only the peripheral field is advantageous over the conventional approaches as it would permit sharply focused images of the central field to continue to reach the fovea, hence the wearer can continue to enjoy clear central, foveal vision necessary for good visual acuity (e.g. for driving, reading, watching TV, etc). This is the main principle of this present invention and is explained in greater details with FIGS. 4e and 4f.

Figure 4E:
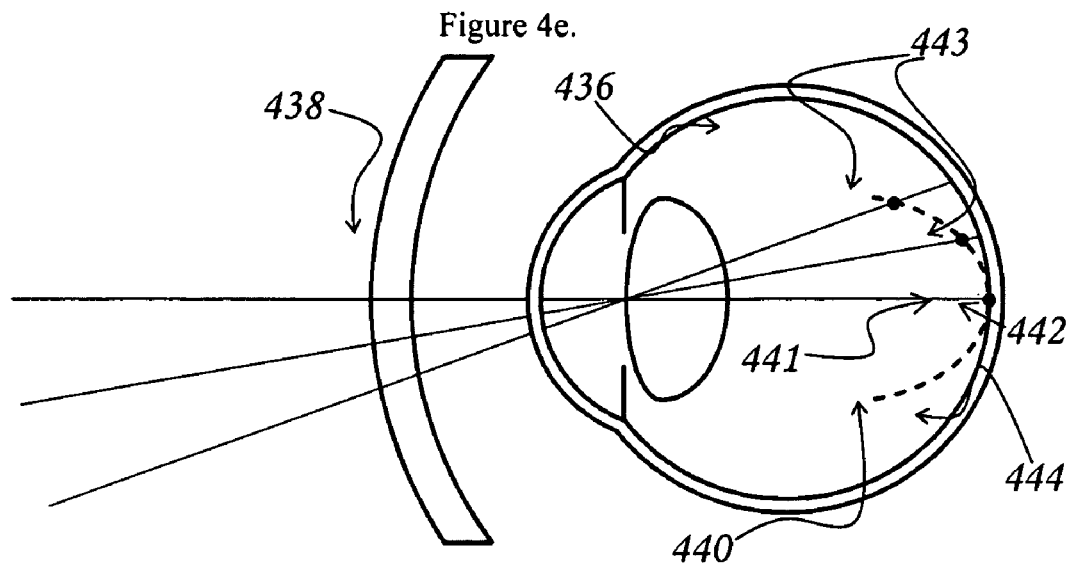
Figure 4F:
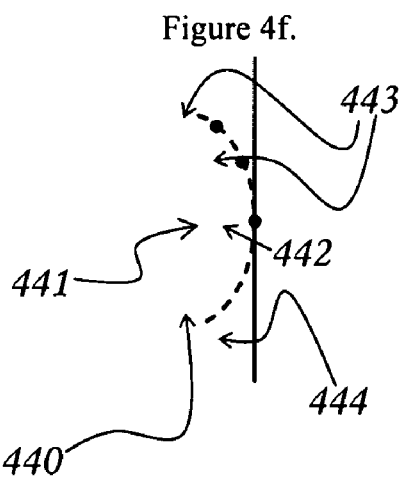

In FIGS. 4e and 4f, an eye [436] with myopic tendencies (i.e. either is myopic, or is non-myopic but would grow into myopia due to factors such as myopic parents or prolonged near work) is prescribed an optical device [438] of the present invention. This optical device [438] is designed so that it would generate a negative relative curvature of field [440] on the eye [436]. This arrangement is advantageous over conventional under-correction approaches as the central, on-axis image point [441] is focused sharply to the fovea [442] enabling good visual acuity. The peripheral image points [443], due to the negative relative curvature of field [440], are focused more anteriorly, or in front (i.e. in the direction against the direction of light in the eye) of the retina [444]. This has the effect of producing a relative under-correction to the peripheral field, which, from our experiment results, would control eye growth and axial elongation. That is, due to the more anterior location of the off-axis, peripheral field image points [443], stimulus to axial growth is significantly reduced, eliminated or reversed in the eye, leading to reduction or elimination of myopia development or reduction and even reversal of myopia progression.

The importance of the peripheral field in driving myopia progression also explains why the conventional approaches of under-correcting the central vision has been shown not to be effective for all people, and in fact in some published studies, have been shown to increase myopia for some individuals.

Figure 4G:
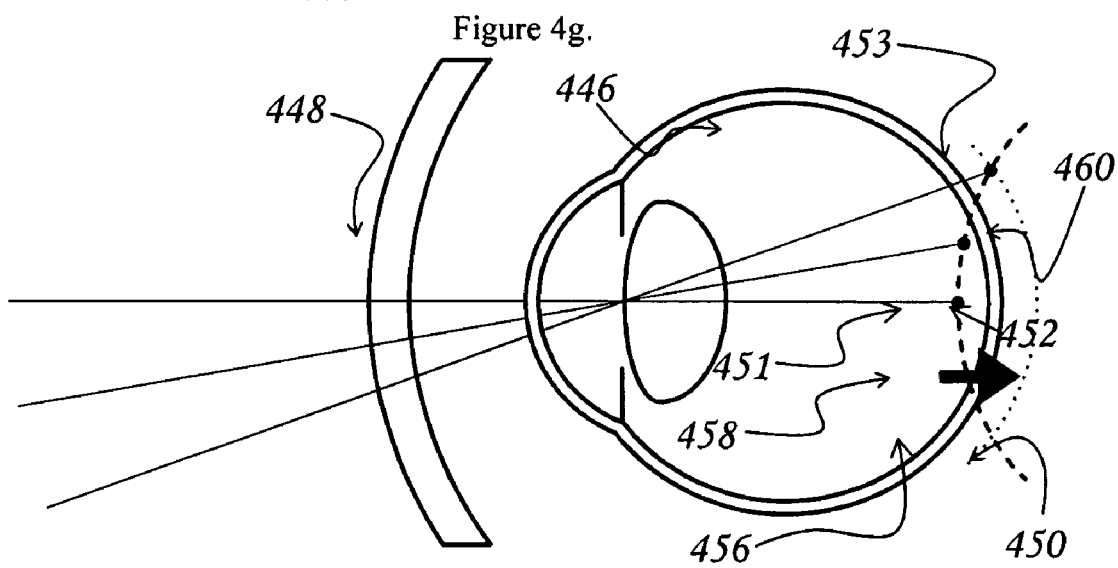
Figure 4H:
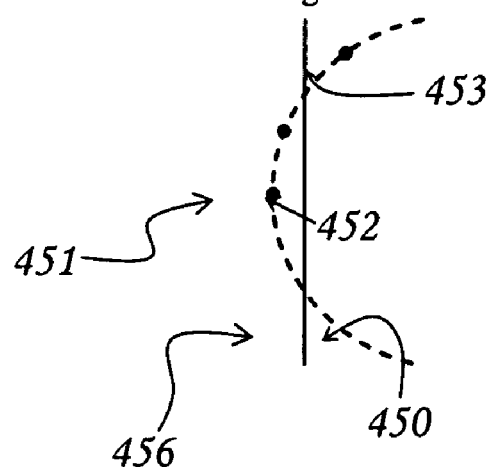

In FIGS. 4g and 4h, an eye [446] has been under-corrected using the conventional approach of under-correction. This eye, with the optic device [448] implementing the conventional approach to provide the under-correction, either together with the optics of the eye, or by itself, also induced a significant amount of positive relative curvature of field [450] to the eye. Hence, while this approach places the central, on-axis image point [451] in front of the fovea [452], in the attempt to reduce the stimulus to growth, due to the positive relative curvature of field [450], the off-axis, peripheral field image points [453] are focused to behind (i.e. in the same direction as the direction of light in the eye) the retina [456]. From our experiment results that demonstrated the effectiveness of the periphery of the eye to drive axial growth, these over-corrected peripheral image points induce a stimulus for axial elongation (as indicated by the arrow [458]) leading to eye growth [460] and progression of myopia, despite the efforts made to control the central image focus position.

Figure 4I:
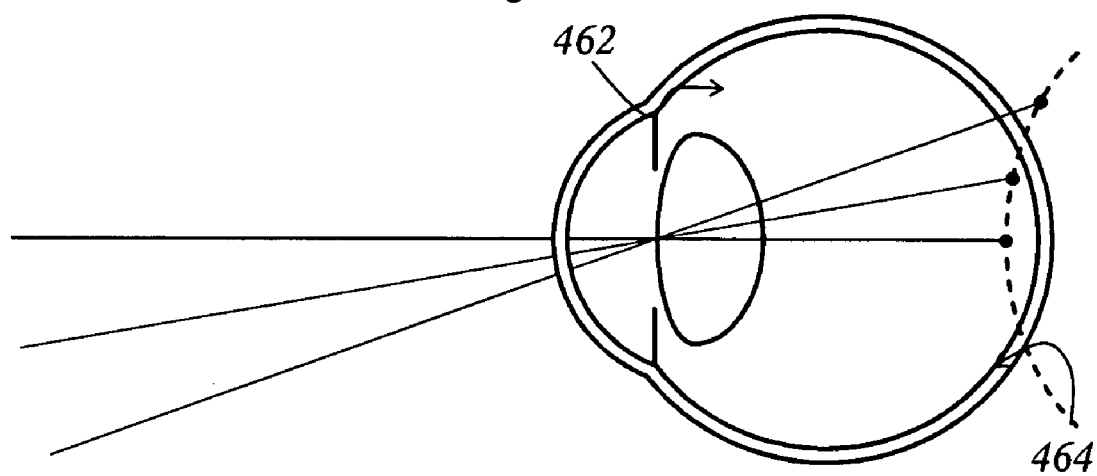
Figure 4J:
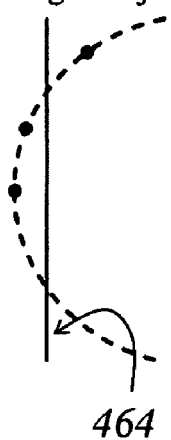
Figure 4K:
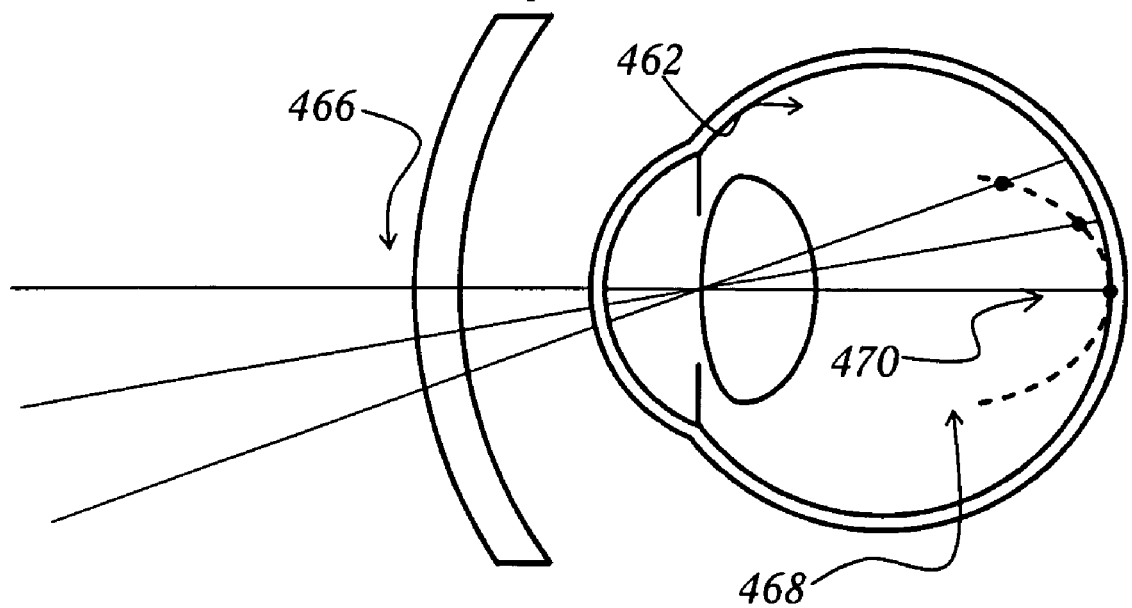
Figure 4L:
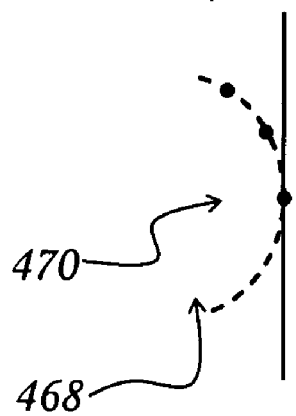

For an eye [462] with relative positive curvature of field [464] (as shown in FIGS. 4i and 4j), an optical device [466] of the present invention may be designed to, in combination with the optics of the eye, provide a sharp central focus [470] as well as a net negative relative curvature of field [468] (as shown in FIGS. 4k and 4l). This returns the optics of the combined eye and optical device system to one similar to that described in FIGS. 4e and 4f, which is effective in eliminating the stimulus for axial growth and myopic progression or development as well as continuing to provide a sharp central focus necessary for good visual acuity.

From the foregoing explanations, it should now be readily understood that a method by which the progression of myopia can be retarded, eliminated or reversed, is by introducing an optical device, including spectacles, contact lenses, artificial corneal devices such as on-lays and in-lays, corneal implants, anterior chamber lenses or intraocular lenses, or by employing interventions, such as methods for corneal and epithelial remodeling and sculpting including orthokeratology and refractive surgery such as epikeratophakia, thermokeratoplasty, LASIK, LASEK and PRK, that can provide a resultant negative relative curvature of field at the retina, and that in addition, in order to continue to provide good central visual acuity for critical visual tasks, the optical device or optical intervention should ensure good focus of central field image to the retina.

It is important to note that, while the appropriate type of refractive defocus can drive eye growth (or non-growth) leading to myopia (or its regression) in the phenomenon of lens compensation, when the amount of refractive defocus is great, there may be such a large degradation in image quality due to the severe defocus that the optical state may change into the phenomenon of form deprivation and may induce myopia in that way. For example, when an image is placed anterior to the retina by the introduction of a +0.5 D lens, stimulus to axial elongation is removed and myopia may be controlled. Should the image be placed extremely anteriorly, however, for example, by using a +5 D lens, the image degradation at the retina may be so great that the condition becomes one of form deprivation and may lead to the development or propagation of myopia. In such cases, myopia is induced rather than reduced despite the use of positive powered lenses and despite the visual image being anterior to the retina. This change from lens compensation effect to form deprivation effect may apply whether the image is located centrally or peripherally in terms of field angles. Hence, for the present invention to be effective, the minimum amount of relative negative curvature of field at the peripheral field angles must be sufficient to eliminate the stimulus for axial elongation, while the maximum amount of relative negative curvature of field must not be so great as to cause severe degradation of the peripheral visual image and bring about form deprivation myopia. We consider the minimum amount of relative curvature for effective treatment to be around the spherical equivalent (i.e. the refractive state as measured at the circle of least confusion) of +0.25 D to +0.50 D. We consider the maximum amount of relative curvature of field before substantial vision degradation occurs, which leads to form deprivation myopia, to be around the spherical equivalent of +3.50 D to +4.00 D, which represents the upper limit for negative curvature of field for effective treatment of myopia.

Figure 5A:
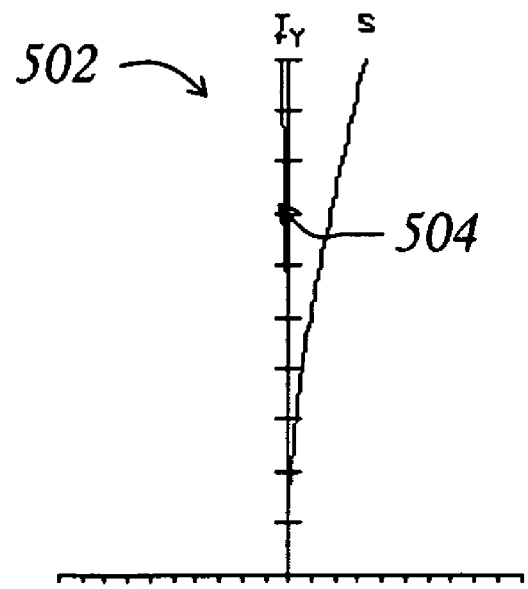
FIGS. 5a to 5c are relative curvature of field graphs and optical ray-tracing diagrams illustrating the principle of one embodiment of the present invention, implemented as a spectacle lens design, employing lens surfaces described by conic sections. The example spectacle lens design is suitable for retarding, ceasing or reversing the progression of myopia for a −3 D myope.
Figure 5B:
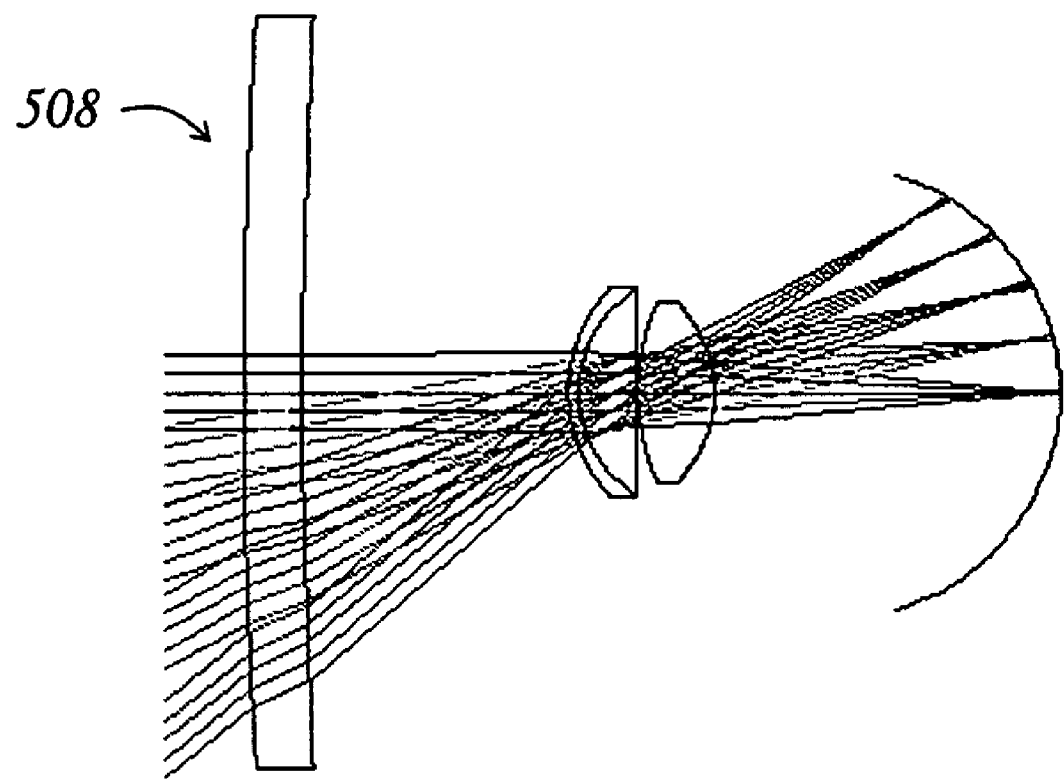
Figure 5C:
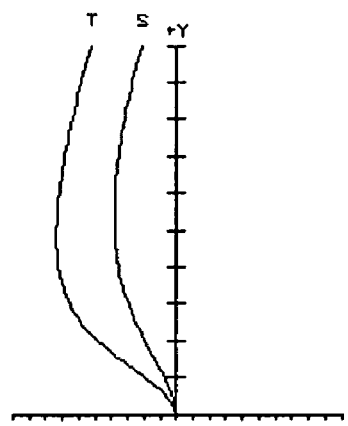

One implementation of the present invention is the use of spectacles with lenses designed to deliver the appropriate amount of negative relative curvature of field. One example of such a spectacle lens implementation is illustrated in FIGS. 5a to 5c. When an eye with −3 D of axial myopia is corrected with a standard spectacle lens (for example, with only spherical surfaces) of the correct power, but which does not attempt to control or modify the curvature of field of the eye-lens combination, the resultant relative curvature of field at the retina of this example eye may be positive, similar to that shown in FIG. 5a. Typical of many optical systems, including this particular eye, for the peripheral field angles, substantial amounts of radial astigmatism (a type of peripheral aberration) exist. This is shown by the existence of two curves plotted for the curvature of field in FIG. 5a. The one labeled "T" [502] represents the focal positions and relative curvature of field for the "tangential" line focus of the radial astigmatism and the one labeled "S" [504] represents the focal positions and relative curvature of field for the "sagittal" line focus of the radial astigmatism, as understood by those skilled in the art.

As understood by eye-care practitioners, astigmatism may be categorized as "simple" astigmatism, "compound" astigmatism or "mixed" astigmatism. Simple astigmatism occurs when one (either sagittal or tangential) of the line foci is positioned on the retina while the other is positioned either in front of (in the case of myopic simple astigmatism) or behind (in the case of hypermetropic simple astigmatism) the retina. Compound astigmatism occurs when both sagittal and tangential line foci are positioned on the same side of the retina, whether both in front of, or both behind the retina. For example, compound hypermetropic astigmatism occurs when both line foci are positioned behind the retina. Mixed astigmatism occurs when one line focus is positioned in front of the retina while the other line focus is positioned behind the retina. In such cases, the eye is hypermetropic along one meridian of astigmatism and myopic along the other meridian, hence the term "mixed".

Experiments on myopia progression using astigmatic lenses have shown that when substantial mixed astigmatism is present, the eye would tend to grow in an effort to reposition the retina at the line focus which is more posteriorly located (i.e. the line focus located behind the retina). Whereas in compound hypermetropic astigmatism, where both foci are posteriorly located, growth of the eye acts to reposition the retina primarily towards the line focus nearer the retina (i.e. the more anteriorly positioned line focus); although in some instances, the eye does grow beyond the line focus nearer the retina and continue on towards the more posteriorly located line focus.

Thus in the case of FIG. 5a, since the peripheral tangential focus [502] is slightly more anteriorly positioned than the retina, while the peripheral sagittal focus [504] is more posteriorly positioned, the eye would experience a stimulus for axial elongation towards the sagittal focus [504] causing eye growth and progression of myopia.

An example of a preferred spectacle lens design of the present invention, as shown in the computer-assisted optical modeling program output of FIG. 5b, in addition to providing the correct refractive power (−3 D), also provides the appropriate control of relative curvature of field at the retina suitable for controlling progression of myopia. This particular exemplary spectacle lens [508] makes use of aspheric lens surfaces with conic sections and is made of glass of refractive index 1.5168 with a central thickness of 3 mm. The back surface of this spectacle lens has an apical radius ($r_o$) of 80 mm with an asphericity (shape factor, p) of −893 while the front surface has an apical radius ($r_o$) of 259.5 mm with a shape factor (p) of −165.6.

The resultant relative curvature of field of the lens and myopic eye combination is shown in the relative field curvature graph of FIG. 5c. As can be seen, both of the astigmatic focal positions are now located anterior to the retina removing any stimulus for axial elongation, thus eliminating, and in some myopes reversing, the progression of the eye's myopia.

As a note on conventional spectacle lens design strategies, due to the limited degrees of freedom (of manipulating lens surface shape, lens thickness and refractive index of the glass material), lens designers are constrained to being able to control either only radial astigmatism or curvature of field, but not both. The conventional philosophy to spectacle lens designs is to control and minimize or eliminate radial astigmatism for two reasons. Firstly, it is generally accepted that vision degradation is more pronounced with astigmatism then curvature of field and, secondly, the belief that in the presence of curvature of field, the eye is able to accommodate to shift the peripheral focal images onto the retina as required. For the purpose of the present invention, control of the curvature of field in the lens design is of priority over control of astigmatism as it is this former aberration that is effective in influencing myopia development and progression. Further, since the photo-receptor cell density at the periphery of the retina is low resulting in a significantly lower acuity in the peripheral field, the design approach of the present invention would not significantly impact vision in the peripheral field.

Figure 6A:
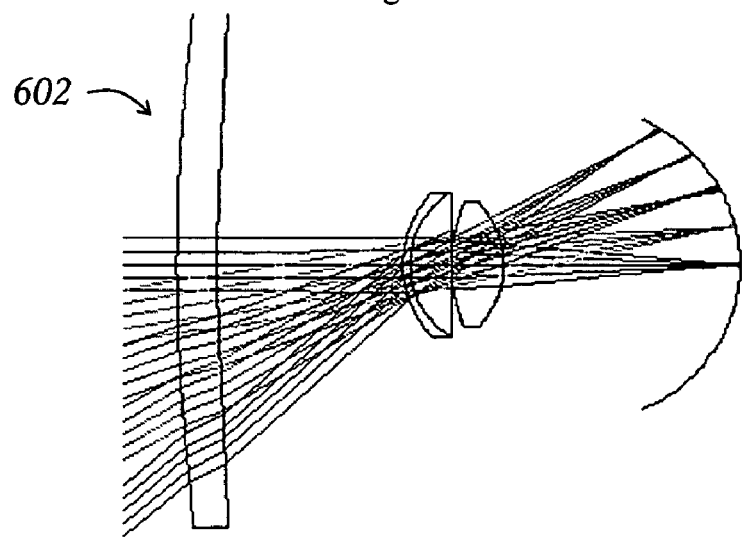
FIGS. 6a to 6d illustrate another embodiment of the present invention, as a spectacle lens design implemented by the use of a combination of conic sections and polynomial equation surface descriptions. The example designs are suitable for retarding, ceasing or reversing the progression of myopia for a −3 D myope.
Figure 6B:
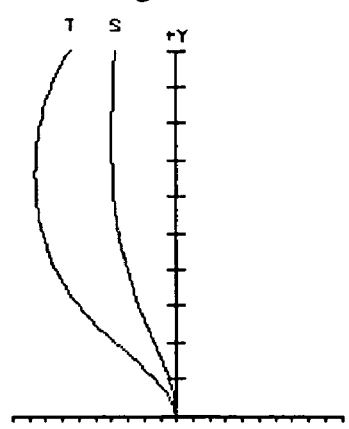

As one skilled in optical engineering and lens design would immediately appreciate, a conic section type aspheric lens is not the only design approach that could achieve the relative negative curvature of field. Any surfaces or optical designs that produce the necessary relative curvature of field when used in combination with the eye may be employed. In FIG. 6a, the surfaces of a spectacle lens of the present invention [602] were designed using a combination of conic section and polynomial equations. This lens has a back surface consisting of a conic section type surface with apical radius ($r_o$) of 75 mm and shape factor (p) of −425. Its front surface is described by a polynomial equation of the form $s=a_1 \cdot x^2 + a_2 \cdot x^4 + a_3 \cdot x^6$ where s is the sagittal height (measured along the axis in millimeters) of the surface relative to its apex (or vertex) and x is the radial distance away from the axis of the lens in millimeters. In this design, $a_1=0.003312$, $a_2=2.053\times10^{-6}$ and $a_3=-6.484\times10^{-9}$. The central thickness of this lens is 3 mm and is made of glass with refractive index 1.517. This particular example design is also suitable for a −3 D myope. The resultant relative field curvature graph for this spectacle lens is shown in FIG. 6b. From this plot, it is clear that stimulus for axial elongation, which leads to myopia initiation or progression, has been removed since both the tangential and sagittal focal positions have been placed anterior to the retina.

In the previous two examples of preferred spectacle designs, both the tangential and sagittal line foci of radial astigmatism were manipulated so as to be positioned substantially in front of the retina to maximize the elimination of stimulus for axial elongation. However, within the present invention, reduction in stimulus for axial elongation, and thereby prevention of initiation or reduction in progression of myopia can be achieved as long as the sagittal (the more posteriorly positioned) line focus is not positioned posteriorly to the retina. Thus, elimination of the stimulus for axial elongation can be achieved even when the sagittal line focus is placed on the retina.

Figure 6C:
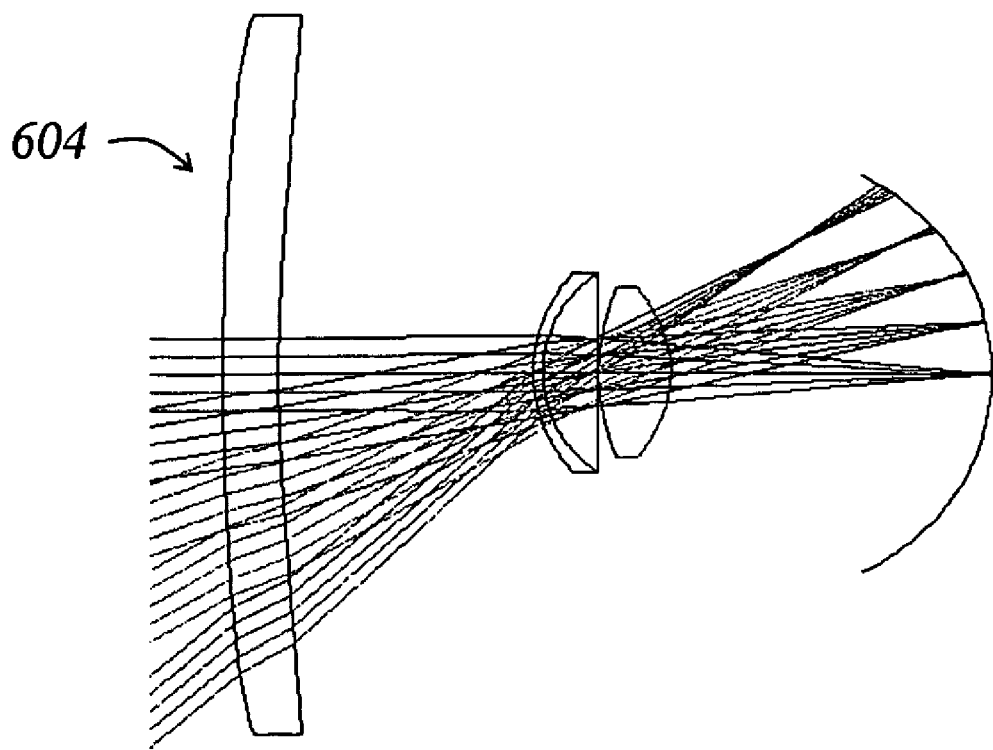
Figure 6D:
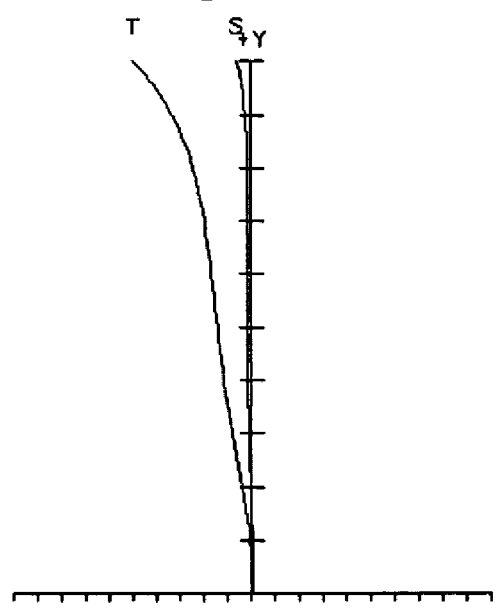

In FIG. 6c, the surfaces of a spectacle lens of the present invention [604] were designed with the particular objective of manipulating the sagittal (more posterior) line focus so that the line focus lies substantially on or only very slightly in front of the retina. This lens, using a combination of conic section and polynomial equations, has a back surface consisting of a conic section type surface with apical radius ($r_o$) of 75 mm and shape factor (p) of −122.8. Its front surface is described by a polynomial equation of the form $s=a_1 \cdot x^2 + a_2 \cdot x^4 + a_3 \cdot x^6$ where s is the sagittal height (measured along the axis in millimeters) of the surface relative to its apex (or vertex) and x is the radial distance away from the axis of the lens in millimeters. In this design, $a_1=0.003285$, $a_2=-4.488\times10^{-6}$ and $a_3=1.631\times10^{-8}$. The central thickness of this lens is 3 mm and is made of glass with refractive index 1.517. This particular example design is also suitable for a −3 D myope. The resultant relative field curvature graph for this spectacle lens is shown in FIG. 6d. From this plot, it can be seen that the tangential line focus has been manipulated to be positioned anteriorly to the retina while the sagittal focus now lie substantially on or slightly in front of the retina. Since neither line foci are located behind the retina the stimulus for axial elongation, which leads to myopia initiation or progression, has been removed. Moreover, under the "sign of defocus" theory of myopia development, which states that the type of defocus (whether relatively more positive or more negative in power) introduces a directional stimulus for growth (i.e. decrease or increase in growth), the myopic defocus associated with the line focus positioned in front of the retina (in that above example, the tangential line focus) would serve as a positive stimulus to reduce growth.

This example design provides the benefit of giving the eye good peripheral visual performance as one of the line focus is on the retina. In comparison, the previous two example designs provide the benefit of greater reduction of stimulus for axial elongation since both the tangential and sagittal line foci have been placed anterior to the retina.

All ensuing example designs aim to place both line foci in front of the retina to maximize the elimination of the stimulus for axial elongation. However, given the above examples, it should now be clear to those skilled in optical engineering and lens design that by the judicious choice of design parameters, either elimination of the stimulus for axial elongation may be maximized (by the anterior positioning of both line foci), or better peripheral visual performance may be achieved but still with the benefit of some reduction of stimulus for axial elongation (by the positioning of the more posterior line focus on or very slightly in front of the retina).

Figure 7A:
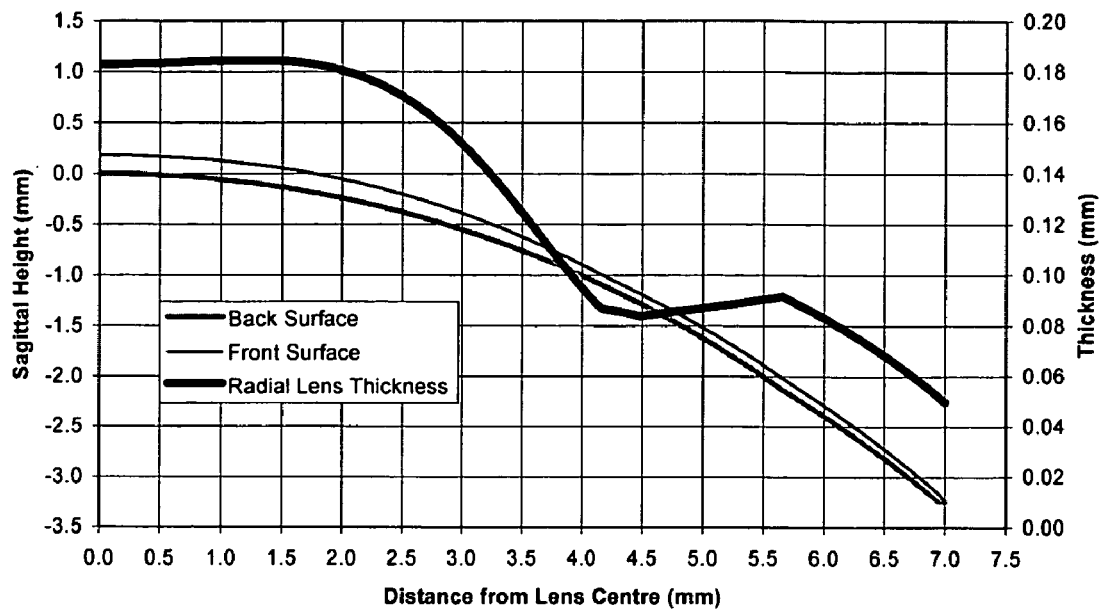
FIGS. 7a and 7b illustrate yet another embodiment of the present invention, as a contact lens.
Figure 7B:
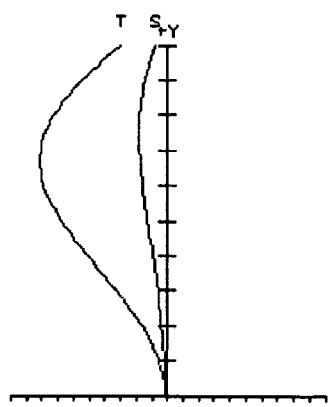

Optical correction devices other than spectacles may also be used under the present invention to control myopia. In particular, those optical correction devices that remain substantially relatively co-axial with the axis of the eye regardless of direction of gaze are more preferred. Therefore, a more preferred method for implementation of the present invention is by the use of soft contact lenses. In FIG. 7a, one example of a soft contact lens design of the present invention is shown by a contact lens design program plot of its front and back surface sagittal heights and its thickness profile along one half-meridian. This soft contact lens design makes use of a combination of conic sections and polynomial equations for its optical zone surfaces. The back surface consists of a conic section type surface with apical radius ($r_o$) of 8.33 mm and shape factor (p) of 0.75. The basic front surface is a conic section with apical radius ($r_o$) of −0.615 mm and shape factor (p) of 0.007 with additional sagittal height added to this basic surface described by a polynomial equation of the form $s=a_1 \cdot x^2 + a_2 \cdot x^4 + a_3 \cdot x^6$ where s is the additional sagittal height (measured along the axis in millimeters) of the surface relative to the basic conic section surface and x is the radial distance away from the axis of the lens in millimeters. In this design, $a_1=0.8695$, $a_2=0.004632$ and $a_3=3.470\times10^{-5}$. This lens has a center thickness of 182 μm, an optic zone diameter (OZD) of 8.2 mm and is suitable for the correction and treatment of a −3 D myope. Although any of a range of contact lens materials may be used, this exemplary lens is assumed to be made from a silicone hydrogel material, which is well known by those skilled in contact lens practice, for its high oxygen permeability suitable for extended or continuous wear, and has a refractive index of 1.427. The resultant relative field curvature graph of this soft contact lens is shown in FIG. 7b. From this plot, it is clear that stimulus for axial elongation, which leads to myopia initiation or progression, has been removed since both the tangential and sagittal focal positions have been placed anterior to the retina.

Figure 8A:
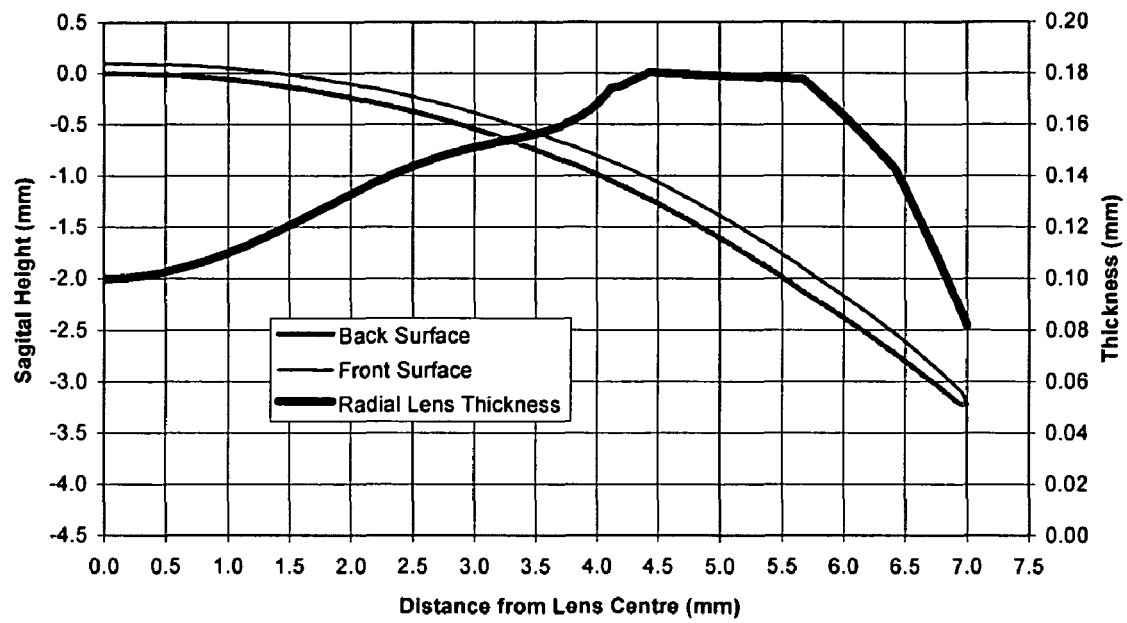
FIGS. 8a and 8b illustrate yet another embodiment of the present invention, as a contact lens.
Figure 8B:
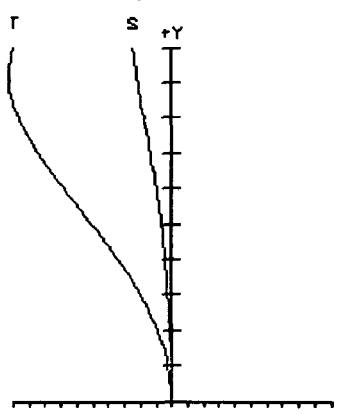

It would become clear from the foregoing that the myopia treatment method and devices of the present invention could be implemented into the correction for any amount of myopia. For example, a soft contact lens design of the present invention suitable for a −10 D myope is shown in FIG. 8a. The back surface of this lens design consists of a conic section type surface with apical radius ($r_o$) of 8.45 mm and shape factor (p) of 0.75. The front surface can be described by a basic spherical surface of radius (r) of 1347.6 mm with additional sagittal height added to this basic surface described by a polynomial equation of the form $s=a_1 \cdot x^2 + a_2 \cdot x^4 + a_3 \cdot x^6 + a_4 \cdot x^8$ where s is the additional sagittal height (measured along the axis in millimeters) of the surface relative to the basic spherical surface and x is the radial distance away from the axis of the lens in millimeters. In this design, $a_1=0.04803$, $a_2=5.740\times10^{-4}$, $a_3=1.543\times10^{-5}$ and $a_4=-1.219\times10^{-6}$. This lens has a center thickness of 100 μm, an optic zone diameter (OZD) of 8.2 mm, and is made of a contact lens material of refractive index 1.427. The resultant relative field curvature graph for this soft contact lens is shown in FIG. 8b. From this plot, it is clear that stimulus for axial elongation, which leads to myopia initiation or progression, has been removed since both the tangential and sagittal focal positions have been placed anterior to the retina.

Given the foregoing discussion, one skilled in optical engineering or lens design would immediately appreciate that the approach of the present invention for retarding the progression of myopia while simultaneously correcting myopia can be applied with different refractive power to different meridians of the same optical device in order to correct refractive astigmatism.

It is important to note the difference between contact lens designs of the current invention and those of a concentric (and especially, center-distance type) bifocal contact lens. While center-distance concentric bifocal contact lenses have powers in the periphery which may mimic the higher positive power required in order to achieve the correct relative curvature of field, the bifocality (i.e. having two effective refractive power, and hence two foci simultaneously) of such contact lenses render them comparatively ineffective for myopia control as explained in FIGS. 9a to 9c.

Figure 9A:
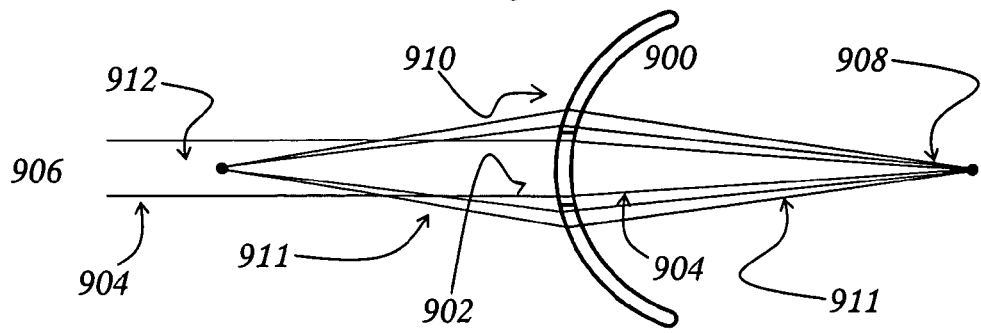
FIGS. 9a to 9c are diagrams explaining, under the principle of the present invention, the basis for the relative inefficacy of concentric bifocal contact lenses and similar conventional approaches for attempting to prevent the progression of myopia.

As illustrated in FIG. 9a, a center-distance concentric bifocal contact lens [900] has a central circular zone [902] that focuses light [904] from distant visual objects [906] to the fovea [908] (central retina) and an outer concentric annular zone [910] surrounding the central zone [902] that simultaneously focuses light [911] from near visual objects [912] also to the fovea [908]. It is due to the simultaneous focusing action of such contact lenses that they are called "simultaneous vision" bifocals. Such simultaneous vision, concentric bifocal contact lenses are typically used for the correction of presbyopia.

In practice, concentric bifocal contact lenses may be center-distance (as described afore) or center-near. The center-near concentric bifocals are more commonly used due to the advantages of compliance with a smaller pupil size during near vision (this is due to a natural reflex whereby when the eye focuses for near, the pupil size also decreases).

Figure 9B:
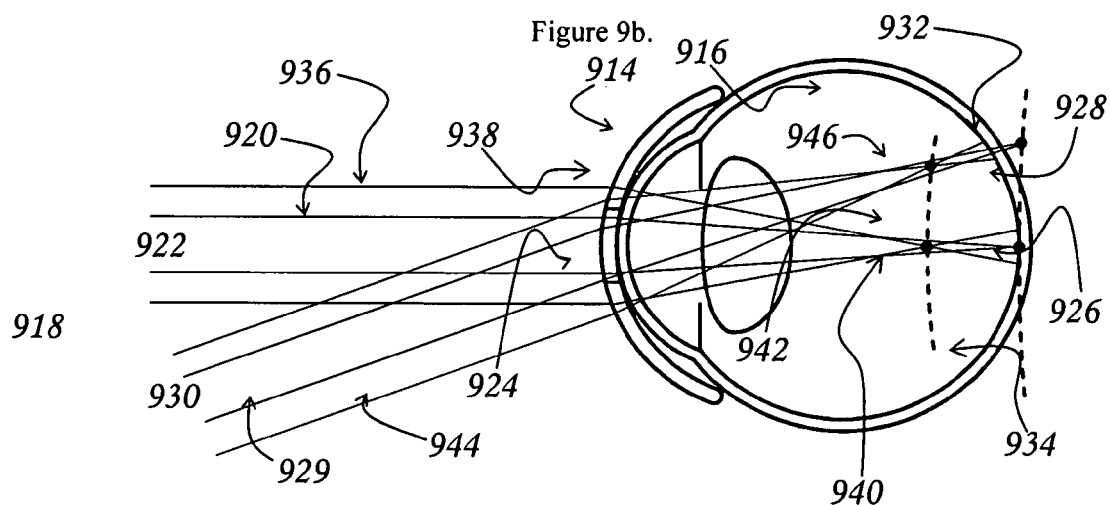
Figure 9C:
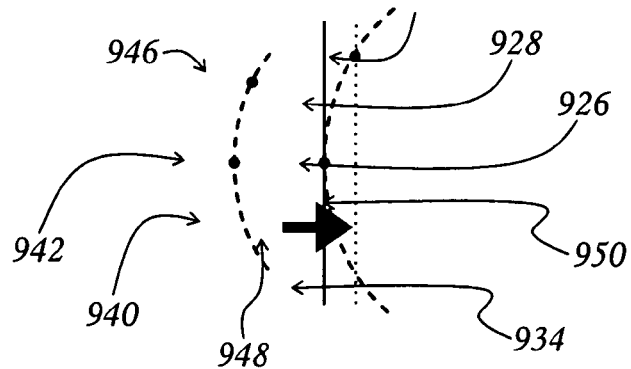

In order to achieve the center-distance (and hence surround-near) focus, such concentric bifocal contact lenses would have peripheral zones of greater positive power than at the central zone. While such lenses may, on cursory observations, be mistakenly identified with a lens which provides a negative relative curvature of field, (center-near concentric bifocals do not resemble the contact lenses of the present invention as they have a more negative power periphery), compared to the designs of the present invention, they are not effective in the control of myopia due to their bifocality as illustrated in FIG. 9b. A center-distance concentric bifocal contact lens [914] is placed on an eye [916] looking at a distant object [918]. Due to the bifocality of the lens [914], two images are formed at all field positions. Thus, light [920] from the central field [922] passing through the central distance optical zone [924] of the contact lens [914] is focused to the fovea [926] and forms a clear image of the object [918]. Due to the presence of relative positive curvature of field [928] in this eye, light [929] from the peripheral field [930] that passes through the central distance optical zone [924] is imaged to a position [932] behind the retina [934]. Simultaneously, light [936] from the central field [922] passing through the annular near optical zone [938] of the contact lens [914] is focused to a near focal point [940] in front of the retina [934] and fovea [926]. This near focal point has its own curvature of field [942] such that light [944] from the peripheral field [930] that passes through the annular near optical zone [938] is imaged to a point [946] lying on the near focus curvature of field [942]. The relationship of the relative curvature of field for the distance and near foci to the retina and fovea is shown in FIG. 9c as a relative field curvature graph. It should also be noted that with the presence of bifocality, the retinal image quality for any object in space will always be degraded regardless of eccentricity due to the constant superpositioning of a clear (distance or near) and a blurred (near of distance respectively) image at the retina, which is also potentially a form-deprivation stimulus for axial growth.

In our experiments, we have shown by the use of astigmatic lenses, which produce two line foci, that when two axial line focal positions are offered to the retina, the eye would tend to grow to one of the line foci rather than the circle of least confusion. In the case of compound hypermetropic astigmatism (in which both axial line foci are positioned behind the retina), the eye would tend to grow to reposition the retina to that of the more anteriorly positioned line focus. In simple hypermetropic astigmatism (in which one line focus is positioned on the retina and the other line focus is positioned behind the retina) eye growth may stabilize and maintain the more anteriorly located focal line on the retina, but in some case the eye would grow to reposition the retina to that of the more posteriorly positioned line focus. In mixed astigmatism (in which one line focus is positioned in front of the retina and the other line focus is positioned behind the retina), the eye would tend to grow to reposition the retina to that of the more posteriorly positioned line focus.

The intention of myopia prevention using bifocal contact lenses is to reduce the amount of accommodation required and/or the amount of defocus incurred without accommodation during near vision by using the near optical zone during near visual work (e.g. reading). However, as seen in FIG. 9c, due to the simultaneous presence of both the distance and near images as well as the positive relative curvature of field, stimulus for eye growth (in the direction of the arrow [948]) towards the distance image surface would lead to axial elongation [950] and the development or progression of myopia. This explains why the use of bifocal contact lenses has not been effective in the control of myopia for all individuals. The control of myopia would be effective by manipulation of the relative curvature of field, as taught in the present invention.

Figure 10A:
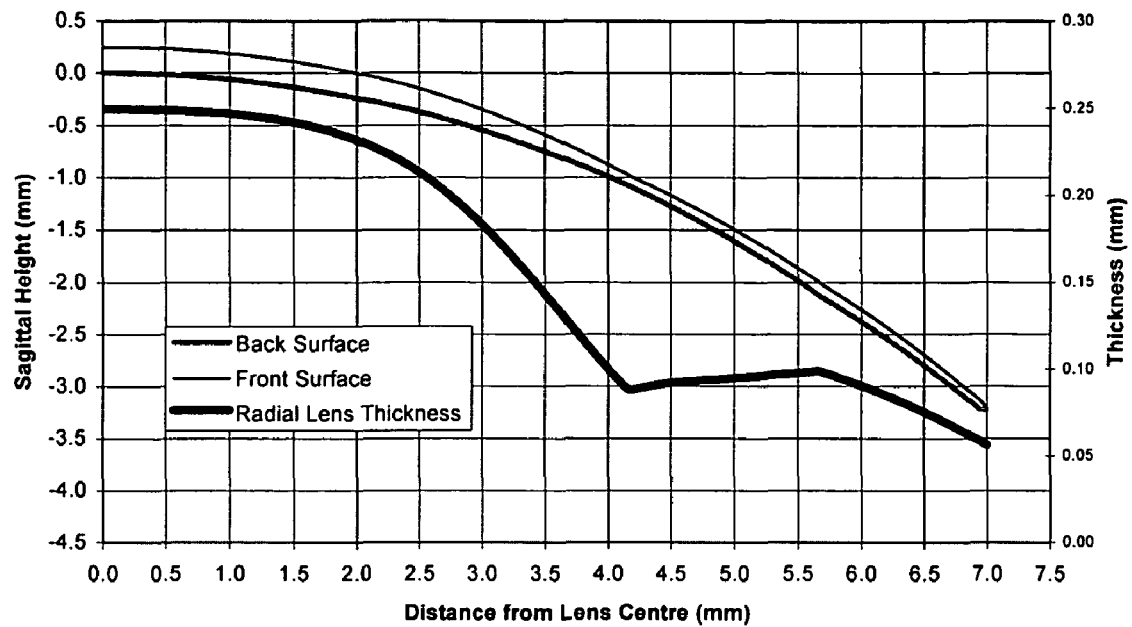
FIGS. 10a and 10b illustrate yet another embodiment of the present invention, as a soft contact lens design to control relative curvature of field that has a plano power suitable for prevention of the development of myopia for a non-myope with myopic tendencies.
Figure 10B:
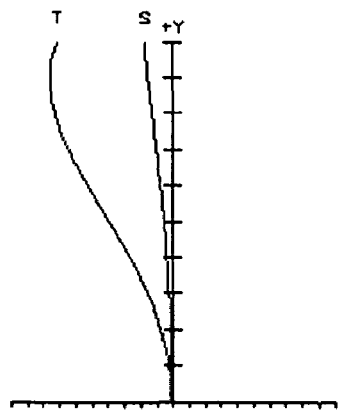

While the present invention may be used to retard or reverse the progression of myopia for an existing myope, it may also be used to prevent the onset of myopia for individuals in the 'at-risk' category; for example, those with myopic parents or who are involved in prolonged near visual tasks (such as studying or computer operation) are known to have a high likelihood of developing myopia. For these individuals who may not be myopic but have myopic tendencies, the present invention may be implemented in a lens with zero refractive power. An example of such a zero-powered lens (also called a "plano" lens by eye-care professionals), which incorporates the present invention's approach to preventing the onset of myopia, is shown in FIG. 10a. The back surface of this lens design consists of a conic section type surface with apical radius ($r_o$) of 8.45 mm and shape factor (p) of 0.75. The front surface is described by a basic spherical surface with a radius (r) of 14.75 mm and with additional sagittal height added to this basic surface described by a polynomial equation of the form $s = a_1 \cdot x^2 + a_2 \cdot x^4 + a_3 \cdot x^6 + a_4 \cdot x^8$ where s is the additional sagittal height (measured along the axis in millimeters) of the surface relative to the basic spherical surface and x is the radial distance away from the axis of the lens in millimeters. In this design, $a_1 = 0.02553$, $a_2 = 5.900 \times 10^{-4}$, $a_3 = 2.564 \times 10^{-5}$ and $a_4 = -1.437 \times 10^{-6}$. This lens has a center thickness of 249.2 μm, an optic zone diameter (OZD) of 8.2 mm and is made of a contact lens material of refractive index 1.427. The resultant relative field curvature graph for this soft contact lens is shown in FIG. 10b. From this plot, it is clear that the stimulus for axial elongation, which can initiate myopia development, has been removed since both the tangential and sagittal focal positions have been placed anterior to the retina.

Figure 11A:
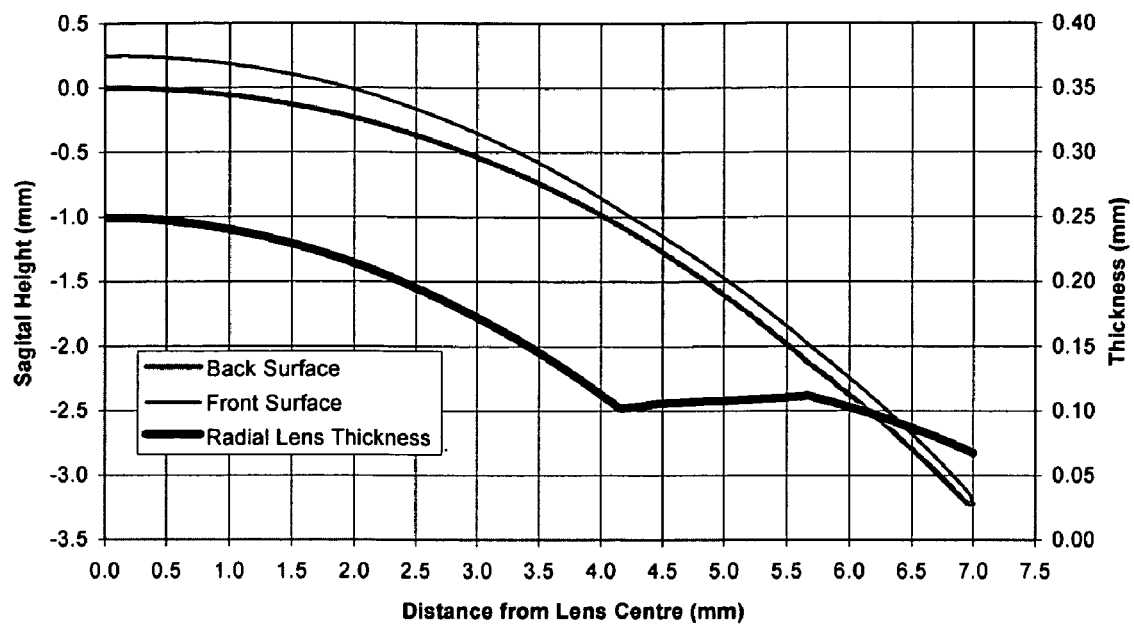
FIGS. 11a and 11b illustrate yet another embodiment of the present invention, as a soft contact lens design of the present invention that controls relative curvature of field to stimulate axial elongation and eye growth in order to reduce hypermetropia bringing the eye back towards emmetropia.
Figure 11B:
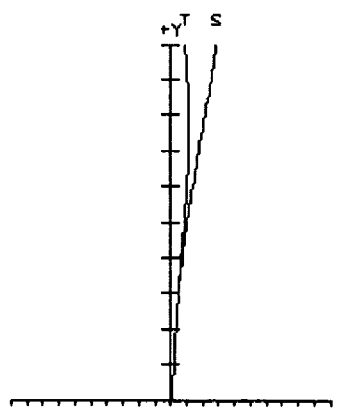

For some individuals and in certain applications, it may be advantageous to be able to stimulate axial elongation. For example, this may be done for a hypermetrope in order to reduce the amount of hypermetropia. One benefit of reducing the amount of hypermetropia in such individuals is improved near focusing ability. The converse of the basic approach of the present invention may be employed to reduce the amount of hypermetropia through induction of eyeball growth. FIG. 11a shows a soft contact lens design of the present invention suitable for returning a +6 D hypermetrope towards emmetropia. The back surface of this lens design consists of a spherical surface with radius (r) of 8.60 mm. The front surface is described by a basic spherical surface of radius (r) of −614.7 mm with additional sagittal height added to this basic surface described by a polynomial equation of the form $s = a_1 \cdot x^2 + a_2 \cdot x^4 + a_3 \cdot x^6$ where s is the additional sagittal height (measured along the axis in millimeters) of the surface relative to the basic spherical surface and x is the radial distance away from the axis of the lens in millimeters. In this design, $a_1 = 0.06605$, $a_2 = 1.400 \times 10^{-4}$ and $a_3 = 6.190 \times 10^{-6}$. This lens has a center thickness of 249 μm, an optic zone diameter (OZD) of 8.2 mm and is made of a contact lens material of refractive index 1.427. The resultant relative field curvature graph for this soft contact lens is shown in FIG. 11b. It can be seen from this plot that both the tangential and sagittal focal positions have now been effectively placed behind (more posterior to) the retina. In this configuration, a stimulus for axial elongation is evoked, which can initiate eye growth leading to reduction of hypermetropia.

FIGS. 12a to 12i illustrate an advanced application of the present invention to partially correct complex optical errors including astigmatism and high-order aberrations while simultaneously manipulating the curvature of field for controlling myopia. This technique in myopia control of the present invention provides for the simultaneous correction of the wave-front aberrations (typically including higher-order aberrations) of the eye while delivering the correct amount of relative curvature of field. This approach can provide further improved vision while maintaining the appropriate stimulus required to retard the progression of myopia.

Figure 12A:
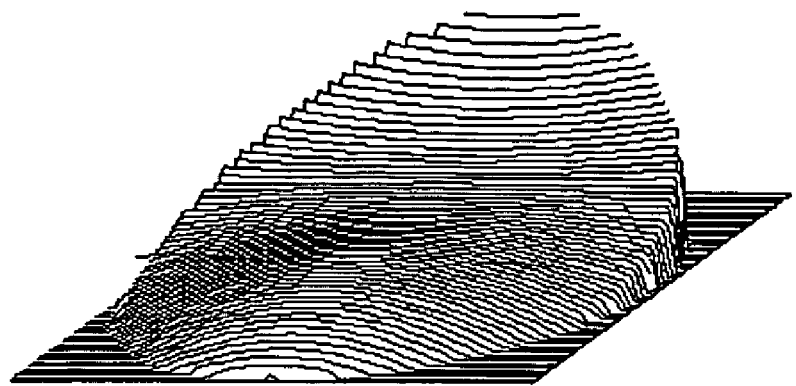
FIGS. 12a to 12i illustrate yet another embodiment of the present invention, an advanced application of a soft contact lens design to control relative curvature of field while simultaneously partially correcting the higher-order aberrations of the eye.

The aberrations (including "astigmatism", a non-spherical optical defect usually correctable using cylindrical corrections in a spectacle or toric contact lenses) and especially higher-order aberrations (such as "coma", a type of aberration, typically not correctable with conventional vision correction devices such as spectacles) of an individual may be measured using a range of existing ocular wave-front sensors (e.g. Hartmann-Shack devices). An example of a map of the wave-front aberration of one individual's eye is shown in FIG. 12a. It can be seen from the asymmetry of this wave-front map that this eye has substantial amounts of astigmatism and coma.

For quantitative analyses, vision scientists and optical engineers may describe wave-front aberrations as a Zernike polynomial series. An additional advantage of this method of describing aberrations is that the Zernike polynomial terms relate to aberration-types familiar to the optical engineer or vision scientist. For example, coefficient $Z_2^2$ is indicative of astigmatism in the optics of the eye and $Z_3^1$ is indicative of the presence of coma in the optics of the eye. For the example shown in FIG. 12a, the amplitude of the Zernike coefficients for astigmatism ($Z_2^2$) is −0.446 μm, and for coma ($Z_3^{-1}$) is −0.344 μm.

Figure 12B:
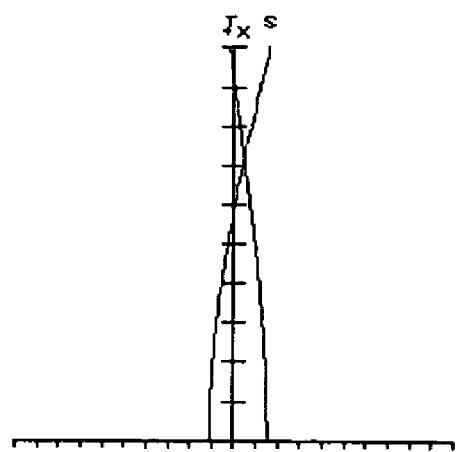
Figure 12C:
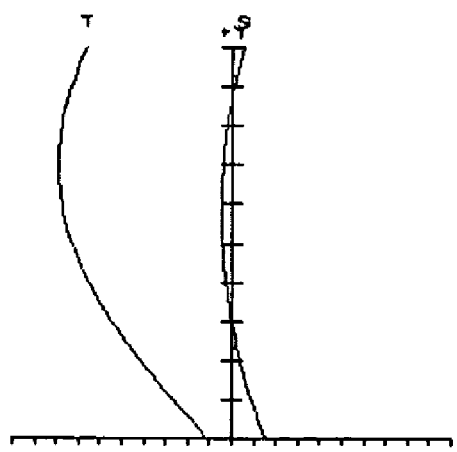
Figure 12D:
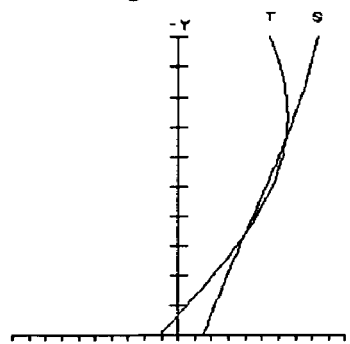
Figure 12E:
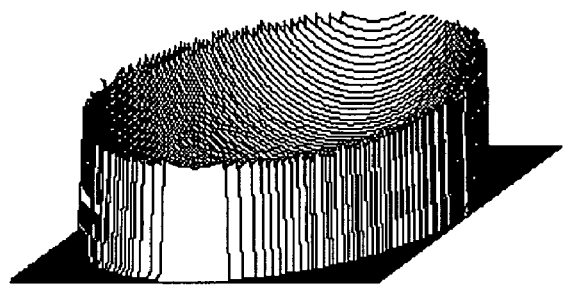

The relative curvature of field native to this individual's eye is shown in FIGS. 12b to 12d. Due to the presence of asymmetric aberrations including astigmatism and coma, the relative curvature of field differs between different meridians. FIGS. 12b, 12c and 12d show the relative curvature of field for the horizontal, upper-vertical and lower-vertical half-meridians respectively. In addition, while this eye is close to being emmetropic in the central field as seen in FIGS. 12b to 12d, the peripheral field image positions for both astigmatic (tangential and sagittal) image surfaces are predominantly located behind the retina along the extent of most of the half-meridians, and would evoke stimulus for axial elongation and eyeball growth leading to myopia development or increase.

An optical device designed according to the principles of the present invention can manipulate the relative curvature of field while partially correcting the higher-order aberrations of the eye. This arrangement would promote the retardation and potential reversal of myopia progression while additionally providing some of the benefits of aberration correction. Such an example is described below and illustrated in FIGS. 12e to 12i. For this particular example, a soft contact lens design was utilized. However, it would be understood by those skilled in the art that any optical devices suitable for the correction of higher-order ocular aberrations would also be suitable. By applying a contact lens design of the present invention to the eye of the described ocular wave-front aberration, the resultant wave-front aberration demonstrates that astigmatism and coma have been effectively eliminated while simultaneously providing the relative curvature of field suitable for controlling myopia development or progression. This is clearly seen in the resultant wave-front map in FIG. 12e. The absence of asymmetry indicates that astigmatism and coma have been effectively eliminated. The amplitudes of the resultant Zernike coefficients associated with the corrected wave-front for astigmatism ($Z_2^2$) and coma ($Z_3^{-1}$) have respectively been reduced to 0.0144 μm and −0.0086 μm demonstrating substantial elimination of astigmatism and coma that would promote improved visual acuity.

Since the wave-front aberration of the eye in this example is rotationally asymmetrical, the contact lens design example is also rotationally asymmetrical (in this case, in order to correct astigmatism and coma) and would need to be maintained in correct orientation (also called "location" by contact lens practitioners) relative to the eye for optimal performance. Design features suitable for the correct orientation of such asymmetrical contact lenses are well known to contact lens practitioners and include prism ballasting, dynamic thin zones, and 'slab-off' designs. Fabrication of asymmetrical design contact lenses is also well known to those skilled in the art and includes the use of computer-controlled multi-axis lathes and mills.

Figure 12F:
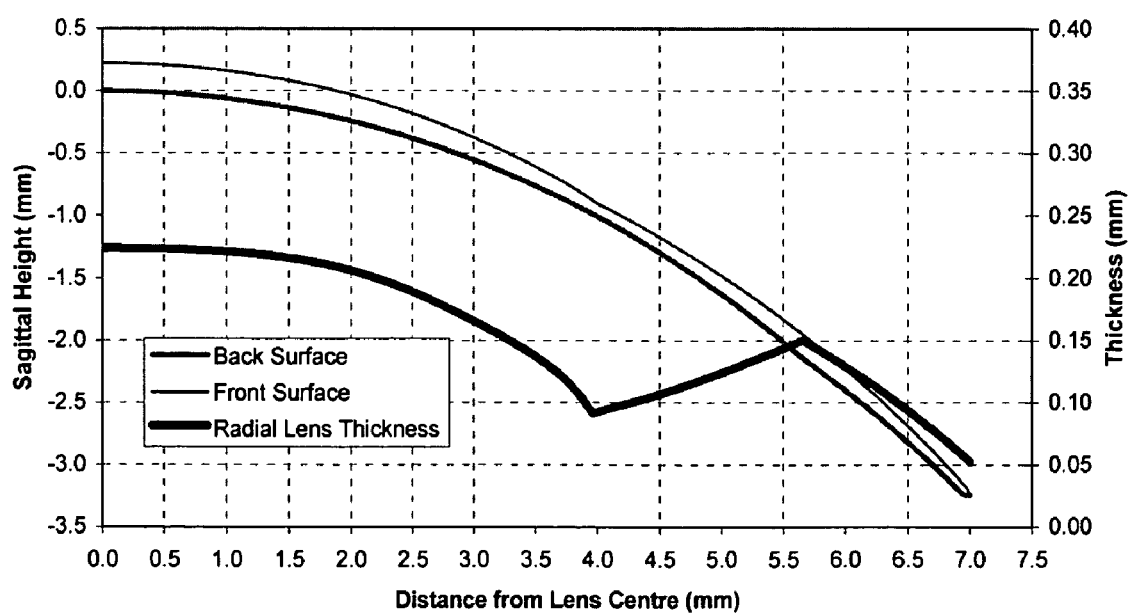
Figure 12G:
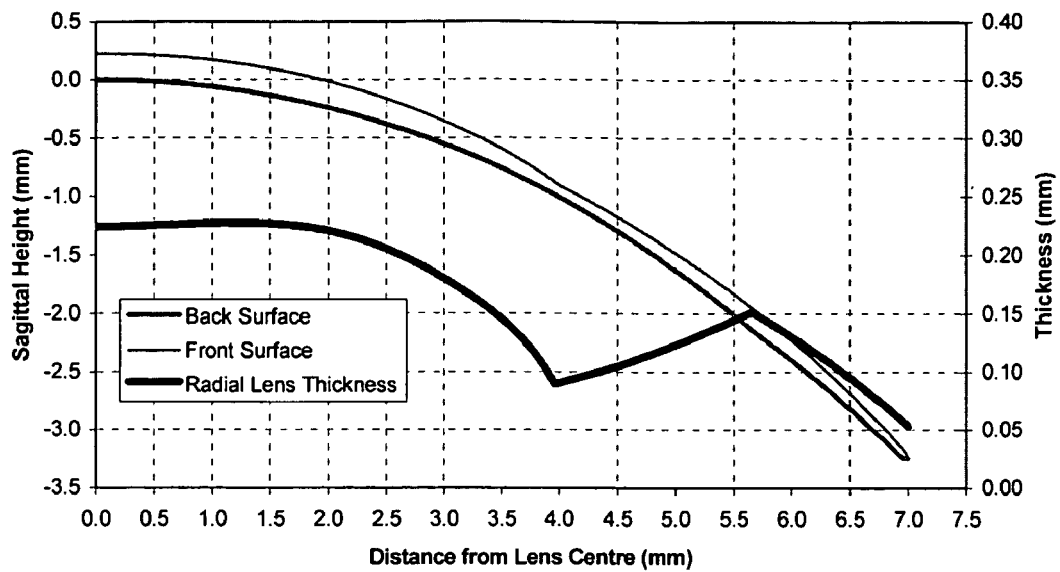
Figure 12H:
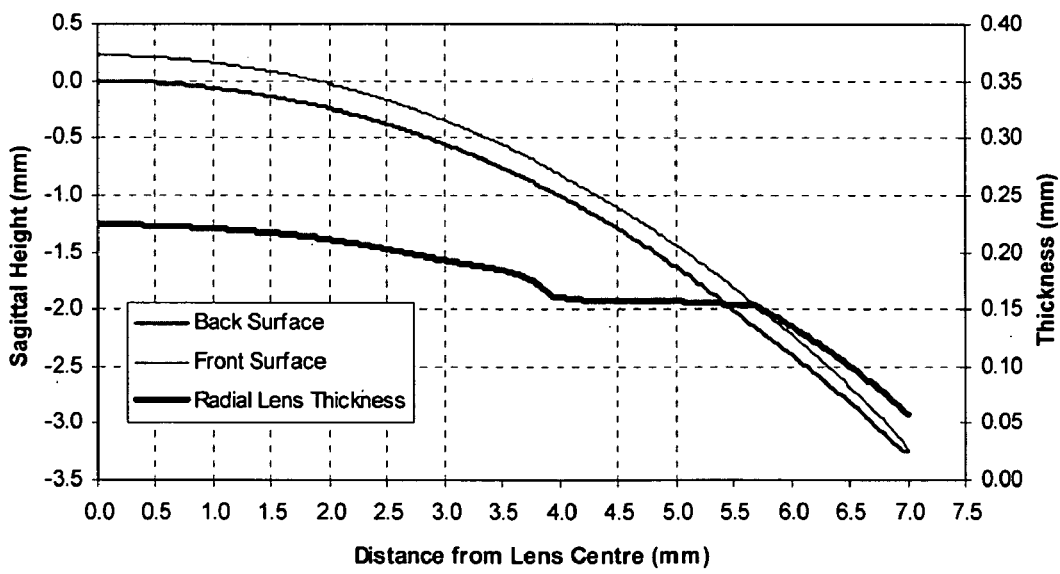

For the wave-front aberration correction components, the optical surface description of such an asymmetrical lens design may be conveniently expressed as a series of Zernike polynomial coefficients. The soft contact lens design of this example is shown in FIGS. 12f to 12h which show contact lens design program plots of its front and back surface sagittal heights and its thickness profile along the horizontal half-meridian (FIG. 12f), the upper-vertical (FIG. 12g) and lower-vertical (FIG. 12h) half-meridians. This soft contact lens design makes use of a combination of conic sections and polynomial equations for its basic optical surfaces. The back surface consists of a conic section type surface with apical radius ($r_o$) of 8.33 mm and shape factor (p) of 0.75. The basic front surface is a conic section with apical radius ($r_o$) of 0.3712 mm and shape factor (p) of 0.004667 with additional sagittal height added to this basic surface described by a polynomial equation of the form $s=a_1 \cdot x^2+a_2 \cdot x^4+a_3 \cdot x^6+a_4 \cdot x^8$ where s is the additional sagittal height (that is, thickness to be added to the surface, measured along the axis in millimeters) of the surface relative to the basic conic section surface and x is the radial distance away from the axis of the lens in millimeters. In this design, $a_1=-1.288$, $a_2=-0.01078$, $a_3=-1.540\times 10^{-4}$ and $a_4=-9.261\times 10^{-6}$. In order to introduce the asymmetrical surface profiles necessary to correct the asymmetrical aberrations, additional sagittal height is further added to this combined conics and polynomial surface described using Zernike polynomials. Specifically, for the front surface design of this example, the Zernike polynomials include tilt ($Z_1^{-1}$), astigmatism ($Z_2^2$) and coma ($Z_3^{-1}$) components with amplitudes of −0.002146 μm, 0.007828 μm and 0.01442 μm respectively.

Figure 12I:
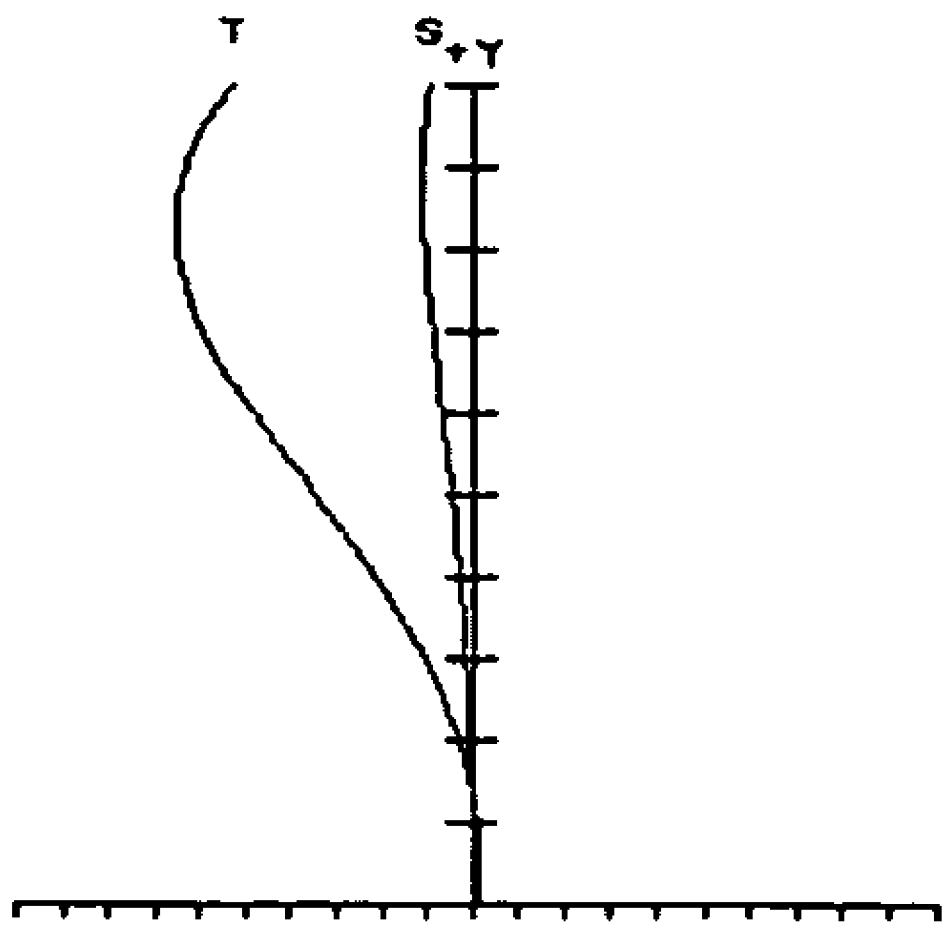

This lens has a center thickness of 224 μm and an OZD of 8.0 mm. This exemplary lens is assumed to be made from a silicone hydrogel material with a refractive index of 1.427. The resultant relative field curvature graph of this soft contact lens is shown in FIG. 12i. Only a single graph is now required to illustrate all meridians as, with the astigmatism and coma effectively eliminated, the resultant relative curvature of field has been rendered rotationally symmetrical. From this plot, it is clear that stimulus for axial elongation, which leads to myopia initiation or progression, has been removed since both the tangential and sagittal focal positions have been placed anterior to the retina.

A recent development, to achieve above-normal vision (or sometimes referred to as "super-vision") is to reduce or eliminate the aberrations of the eye, or the aberrations of the eye and correcting device combined or simply the aberrations of the correction device by producing aberration-corrected designs. It is important to note that such a design approach to achieve super-vision may provide excellent vision but would be insufficient in retarding, eliminating or reversing the progression of myopia in the wearer.

Indeed, current conventional devices that do not control curvature of field are now thought to actually contribute to, or otherwise cause, myopia. In this way, in light of the findings presented in conjunction with the present invention, herein, it is now believed that known, conventional devices could be at least disadvantageous, and potentially harmful in terms of myopia development.

The design of the optical device of the present invention, when applied to also correct ocular aberration, differ substantially from those designed for the optimization of central vision by the correction of aberrations. When a lens is designed to substantially reduce or eliminate the aberrations of the eye, including what are called the "higher order aberrations", such as to provide above-normal visual performance or super-vision, the intention is to optimize wave-front aberration for the central, foveal vision. The reason for the particular attention to central foveal vision is the resolution of the retina (due to the density of the retinal photo-receptors) is densest (providing most acute vision) in this region. Outside this region, the retinal receptor density decreases rapidly to the point where, in the mid-periphery, the density is insufficient to warrant correction of aberrations for improved vision in this region. In contrast, according to the present invention, for the retardation or elimination of myopia progression, the relative curvature of field, governed by the relative positions of image positions across the entirety of the retina including fovea, mid-periphery and periphery, is essential to controlling myopia development and progression.

It will become apparent to those skilled in the field, reading the description of the foregoing embodiments, that the manipulation of the relative curvature of field by optical devices of the present invention may be achieved in several additional ways. For example, instead of the use of conic sections or polynomial equations to define the profiles of the optical surfaces, other surface descriptors may be used including splines, Beziers, Fourier series synthesis, Zernike polynomial as sagittal height descriptors, or combinations of any of the foregoing, or a more general point-by-point surface description via a look-up-table or similar approaches. Further, the design of optical devices of the present invention is not limited to the design of optical surface profiles.

As would be familiar to optical lens designers, at least two additional design variables are available: lens thickness and refractive index. While lens thickness in the range practical for an ophthalmic vision correction device has only a small influence in controlling lens aberrations, it may be manipulated to provide fine control of the lens performance. Thus the thickness of the devices of the current invention is not restricted to the lens thicknesses utilized in the foregoing embodiments.

The refractive index of the device also has a role in the design and control of aberration and optical performance. A large range of materials used in ophthalmic devices may be used for the devices of the current invention. These materials range in refractive index from about 1.33 (e.g. high-porosity material suitable for use in corneal in-lays and on-lays) to about 1.9 (e.g. high-index glass used to produce low-thickness spectacle lenses having a preferred refractive index of about 1.893). Thus the refractive index of the devices of the current invention is not restricted to the refractive indices utilized in the foregoing embodiments.

Further, refractive index can be utilized in a more sophisticated manner. For example, gradient refractive index (GRIN) materials may be used to manipulate the relative curvature of field, as may Fresnel-type optics, holographic or diffractive optics be used, either individually or in combinations with each other or with the surface profile design approaches.

The present invention can be realized in a number of ways, such that an ocular device designed with a prescribed and predetermined amount of suitable peripheral aberrations, in particular relative curvature of field, is provided, and a direct and predetermined refractive change is effected.

The key requirement is that designs of the present invention will afford good visual acuity by ensuring good central field focus to the retina and fovea while simultaneously eliminating the stimulus for axial elongation by positioning the peripheral images in front of the retina by manipulating the relative curvature of field.

The present invention further contemplates that the present methods and apparatuses may be applied to any prescription required to correct the existing refractive error of the eye. For example, a −6 D prescription may be introduced to the device, with the suitable amount of relative curvature of field, thereby providing continued good corrected vision for the −6 D myopic wearer while retarding the progression of his/her myopia.

Naturally, as the amount of myopia becomes reduced, a new corrective device with an appropriately reduced amount of refractive correction (i.e. a lower prescription) would be introduced to maintain parity with the new reduced level of myopia.

The invention may be realized as mass-produced devices, for example by high volume molding technology, or as custom-designed devices. In the case of mass-produced devices, the relative curvature of field may be designed to be suitable for the typical sub-population of myopes. For example, for a mass production −3 D prescription device intended for retarding the progression of −3 D myopes, the design would include compensation for the existing ocular relative curvature of field of a typical −3 D myope. In this way, useful effects can be achieved by population-average mass-produced designs in many individuals.

For a given individual, however, optimal myopia retardation effect is achieved by custom-designed devices. For the custom-designed devices, the actual ocular aberrations including the existing relative curvature of field of the individual intended wearer may be measured, for example using one of a range of available ocular wave-front sensors (e.g. Hartmann-Shack devices) and oblique or off-axis eye-ball axial length measurements using optical coherent tomography (OCT) or other types of interferometers or high-resolution ultrasound systems. The design then takes into account the actual existing relative curvature of field in order to achieve a net negative relative curvature of field while maintaining central field focus.

The present invention further contemplates promoting the return of a hypermetropic eye towards emmetropia. This is realized by the introduction of a suitable amount of positive relative curvature of field into the device, thereby promoting axial elongation and, hence, reduction of hypermetropia.

While the preferred embodiments are in the form of soft or RGP contact lenses, it will be immediately obvious to those skilled in the art that this invention may also be implemented in other forms of contact lenses (e.g. haptic or scleral contact lenses and "piggy-back" systems where two or more contact lenses may be worn in tandem), spectacles, IOLs, artificial corneas (e.g. in-lays, on-lays, keratoprostheses), anterior chamber lenses as well as by methods suitable for corneal or epithelial remodeling or sculpting including orthokeratology and refractive surgery (e.g. epikeratophakia, PRK, LASIK, LASEK, etc.). In the case of RGP or haptic/scleral contact lenses as well as contact lenses used in the application of orthokeratology, the optical design will be manipulated to take into account also the optical influence of the tear-lens (produced by the tear layer between the posterior surface of the contact lens and the anterior corneal surface).

With the potential introduction of active optical devices with the potential to correct refractive error and ocular aberrations in real-time (e.g. wave-front correction systems and 'adaptive optics' systems), it is contemplated that the design approaches of this invention may also be incorporated in those devices.

Many modifications, variations, and other embodiments of the invention will come to the mind of one skilled in the art to which this invention pertains having the benefit of the teachings presented in the foregoing descriptions. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method of altering myopia- or hypermetropia-progression in an eye having a retina comprising the steps of:
    applying a corrective device to said eye, said correcting device comprising an optical configuration for controlling off-axis peripheral aberration and relative curvature field of said device;
    controlling off-axis peripheral aberration of said eye and said corrective device;
    shifting the image of a peripheral visual field relative to a peripheral retina while substantially simultaneously positioning a central image at or near a fovea; and
    providing substantially clear central vision and a signal to modify axial growth.

2. The method of claim 1, wherein the step of shifting the image of the peripheral visual field relative to the peripheral retina further comprises positioning the interval of Sturm partially or entirely in front of the peripheral retina.

* * * * *